(12) United States Patent
Brown et al.

(10) Patent No.: US 10,788,451 B2
(45) Date of Patent: Sep. 29, 2020

(54) BIOCHEMICAL ANALYSIS INSTRUMENT

(71) Applicant: Oxford Nanopore Technologies Ltd., Oxford (GB)

(72) Inventors: Clive Gavin Brown, Cambridge (GB); James Peter Willcocks, Oxford (GB)

(73) Assignee: Oxford Nanopore Technologies Ltd., Oxford (GB)

( * ) Notice: Subject to any disclaimer, the term of this patent is extended or adjusted under 35 U.S.C. 154(b) by 0 days.

(21) Appl. No.: 15/491,450

(22) Filed: Apr. 19, 2017

(65) Prior Publication Data
US 2017/0350859 A1 Dec. 7, 2017

Related U.S. Application Data

(63) Continuation of application No. 14/302,303, filed on Jun. 11, 2014, now abandoned, which is a
(Continued)

(30) Foreign Application Priority Data

Dec. 31, 2009 (GB) .................................. 0922743.0
Oct. 1, 2010 (GB) .................................. 1016614.8

(51) Int. Cl.
*G01N 33/00* (2006.01)
*G01N 33/48* (2006.01)
(Continued)

(52) U.S. Cl.
CPC ..... *G01N 27/44756* (2013.01); *C12Q 1/6869* (2013.01); *G01N 33/48721* (2013.01); *G01N 15/1459* (2013.01); *G01N 15/1463* (2013.01)

(58) Field of Classification Search
CPC ............. G01N 35/00; G01N 27/44756; G01N 33/48721; G01N 15/1459; G01N 15/1463;
(Continued)

(56) References Cited

U.S. PATENT DOCUMENTS

| 4,659,920 A | 4/1987 | Nishiura et al. |
| 5,386,373 A | 1/1995 | Keeler et al. |

(Continued)

FOREIGN PATENT DOCUMENTS

| EP | 1965210 A1 | 9/2008 |
| GB | 2430763 | 4/2007 |

(Continued)

OTHER PUBLICATIONS

EP Opposition against EP 2422198 B1 dated Jul. 7, 2014.
(Continued)

*Primary Examiner* — Brian J. Sines
(74) *Attorney, Agent, or Firm* — Wolf, Greenfield & Sacks, P.C.

(57) ABSTRACT

An analysis instrument comprises plural modules connected together over a data network, each module comprising an analysis apparatus operable to perform biochemical analysis of a sample. Each module comprises a control unit that controls the operation of the analysis apparatus. The control units are addressable to select an arbitrary number of modules to operate as a cluster for performing a common biochemical analysis. The control units communicate over the data network, repeatedly during the performance of the common biochemical analysis, to determine the operation of the analysis apparatus of each module required to meet the global performance targets, on the basis of measures of performance derived from the output data produced by the modules. The arrangement of the instrument as modules interacting in this manner provides a scalable analysis instrument.

18 Claims, 15 Drawing Sheets

Related U.S. Application Data continuation of application No. 13/512,937, filed as application No. PCT/GB2010/002206 on Dec. 1, 2010, now Pat. No. 9,127,313.

(60) Provisional application No. 61/265,488, filed on Dec. 1, 2009.

(51) Int. Cl.
*B01L 3/00* (2006.01)
*C12Q 1/00* (2006.01)
*C12Q 1/68* (2018.01)
*G01N 27/447* (2006.01)
*G01N 33/487* (2006.01)
*C12Q 1/6869* (2018.01)
*G01N 15/06* (2006.01)
*G01N 35/00* (2006.01)
*G01N 15/14* (2006.01)

(58) Field of Classification Search
CPC ........ G01N 15/06; G01N 33/00; G01N 33/48; B01L 3/00; C12Q 1/6869; C12Q 1/00; C12Q 1/68
USPC .............................. 436/43; 422/50, 502, 503
See application file for complete search history.

(56) References Cited

U.S. PATENT DOCUMENTS

| | | |
|---|---|---|
| 5,694,495 A | 12/1997 | Hara et al. |
| 7,001,792 B2 | 2/2006 | Sauer et al. |
| 7,155,344 B1 | 12/2006 | Parce et al. |
| 7,501,279 B2 | 3/2009 | Folch et al. |
| 7,507,575 B2 | 3/2009 | Bedingham et al. |
| 8,461,854 B2 | 6/2013 | Chen et al. |
| 8,828,208 B2 | 9/2014 | Canas et al. |
| 9,057,102 B2 | 6/2015 | Turner et al. |
| 9,127,313 B2 | 9/2015 | Brown et al. |
| 9,546,400 B2 | 1/2017 | Turner et al. |
| 9,556,480 B2 | 1/2017 | Turner et al. |
| 9,651,519 B2 | 5/2017 | Brown et al. |
| 9,678,056 B2 | 6/2017 | Turner et al. |
| 9,738,929 B2 | 8/2017 | Turner et al. |
| 2003/0070923 A1 | 4/2003 | Schroeder et al. |
| 2003/0096418 A1 | 5/2003 | Yamazaki et al. |
| 2004/0040868 A1 | 3/2004 | Denuzzio et al. |
| 2004/0055901 A1 | 3/2004 | Petersen et al. |
| 2005/0006372 A1 | 1/2005 | Murakami et al. |
| 2005/0127035 A1 | 6/2005 | Ling |
| 2006/0019247 A1 | 1/2006 | Su et al. |
| 2006/0105461 A1 | 5/2006 | Tom-Moy et al. |
| 2007/0095671 A1 | 5/2007 | Kovacs |
| 2007/0099191 A1 | 5/2007 | Nair et al. |
| 2007/0218471 A1 | 9/2007 | Kim et al. |
| 2008/0069739 A1 | 3/2008 | Ludwig |
| 2009/0167288 A1 | 7/2009 | Reid et al. |
| 2009/0283412 A1 | 11/2009 | Sansinena et al. |
| 2009/0298072 A1 | 12/2009 | Ju |
| 2010/0035260 A1 | 2/2010 | Olasagasti et al. |
| 2010/0196203 A1 | 8/2010 | Sanghera et al. |
| 2010/0276588 A1 | 11/2010 | Syms |
| 2010/0331194 A1 | 12/2010 | Turner et al. |
| 2011/0053284 A1 | 3/2011 | Meller et al. |
| 2011/0120871 A1 | 5/2011 | Reid et al. |
| 2011/0202280 A1* | 8/2011 | Sikora .................. C12Q 1/6874 702/19 |
| 2011/0287414 A1 | 11/2011 | Chen et al. |
| 2012/0322679 A1 | 12/2012 | Brown et al. |
| 2013/0045872 A1* | 2/2013 | Zhou .................... C12Q 1/6827 506/2 |
| 2013/0071837 A1 | 3/2013 | Winters-Hilt et al. |
| 2013/0078624 A1 | 3/2013 | Holmes et al. |
| 2013/0090248 A1* | 4/2013 | Link .................... B01F 3/0807 506/2 |
| 2014/0296083 A1 | 10/2014 | Brown et al. |
| 2014/0296089 A1 | 10/2014 | Holmes et al. |
| 2014/0308661 A1 | 10/2014 | Holmes et al. |
| 2014/0329693 A1 | 11/2014 | Reid et al. |
| 2014/0346059 A1 | 11/2014 | Akeson |
| 2015/0346149 A1 | 12/2015 | Brown et al. |
| 2016/0040230 A1 | 2/2016 | Akeson |

FOREIGN PATENT DOCUMENTS

| | | |
|---|---|---|
| JP | 10-62426 | 3/1998 |
| JP | 3668799 | 4/2005 |
| WO | WO 1998/001758 A1 | 1/1998 |
| WO | WO 2002/025934 A2 | 3/2002 |
| WO | WO 2002/029402 A2 | 4/2002 |
| WO | WO 2008/042018 A2 | 4/2008 |
| WO | WO 2008/102120 | 8/2008 |
| WO | WO 2009/022152 A1 | 2/2009 |
| WO | WO 2009/077734 A2 | 6/2009 |
| WO | WO 2010/062913 A2 | 6/2010 |
| WO | WO 2010/122293 A1 | 10/2010 |
| WO | WO 2011/067559 | 6/2011 |

OTHER PUBLICATIONS

[No Author Listed] Helicos BioSciences Corporation, "Helicos Genetic Analysis System," Specification Sheet retrieved online at: www.helicosbio.com/Portals/0/Documents/Helicos_SalesSpec.pdf, 4 pages (2008).

Audet et al., Yield Improvement of a Large Area Magnetic Field Sensor Array Using Redundancy Schemes. IEEE Transactions on Very Large Scale Integration (VLSI) Systems. 1997;5(1):28-33.

Branton et al., The potential and challenges of nanopore sequencing. Nat Biotechnol. Oct. 2008;26(10):1146-53. doi:10.1038/nbt.1495.

Inman et al., A high-throughput distributed DNA sequence analysis and database system. IBM Systems Journal, vol. 40(2):464-486 (2001).

Rhee et al., Nanopore sequencing technology: research trends and applications. Trends Biotechnol. Dec. 2006;24(12):580-6. Epub Oct. 19, 2006.

Zagnoni et al., Microfluidic array platform for simultaneous lipid bilayer membrane formation. Biosens Bioelectron. Jan. 1, 2009;24(5):1235-40. doi: 10.1016/j.bios.2008.07.022. Epub Jul. 23, 2008.

PCT/GB2010/002206, Jun. 14, 2012, International Preliminary Report on Patentability.

PCT/GB2010/002206, Apr. 26, 2011, International Search Report and Written Opinion.

U.S. Appl. No. 16/170,620, filed Oct. 25, 2018, Brown et al.

\* cited by examiner

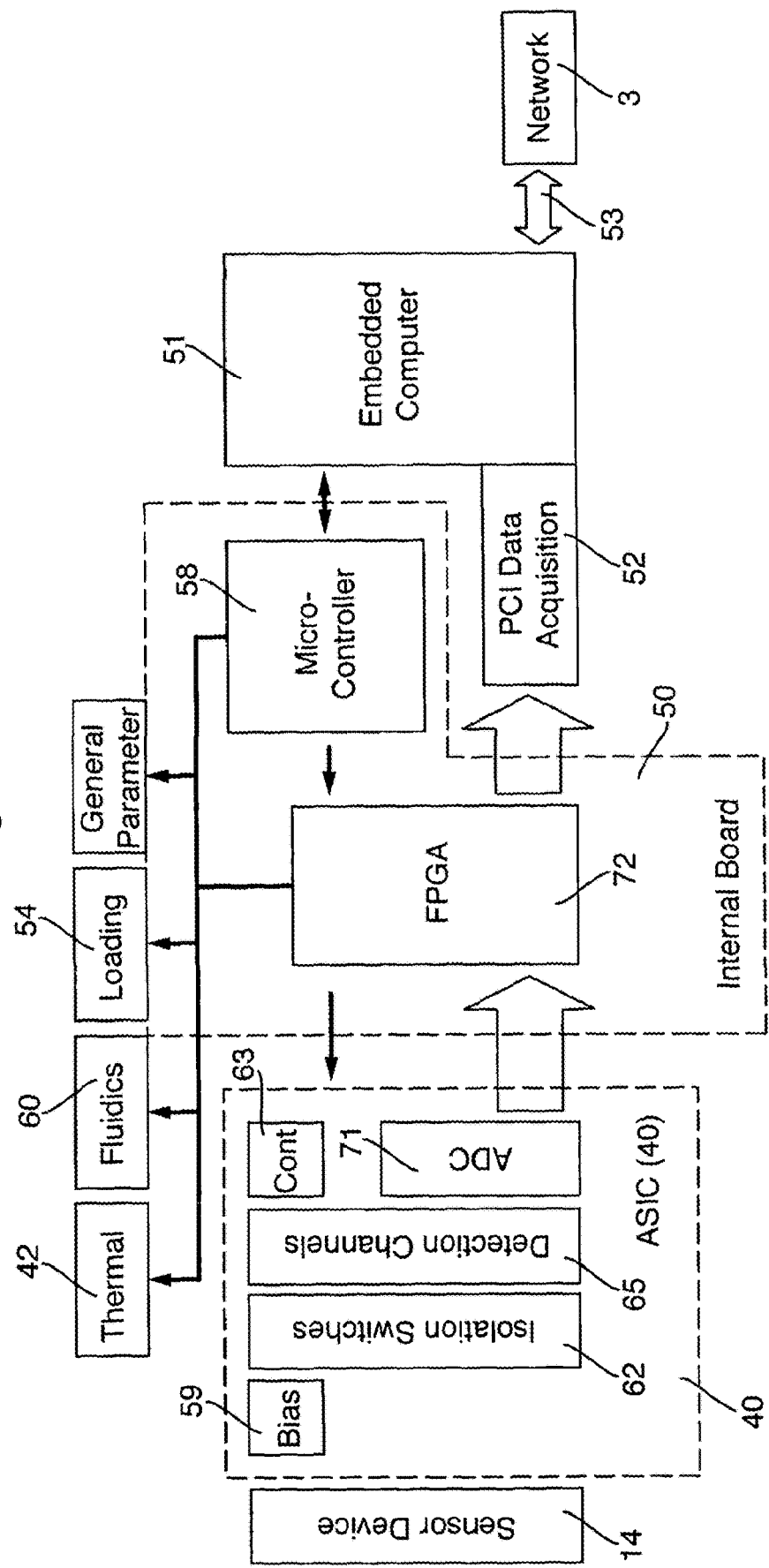

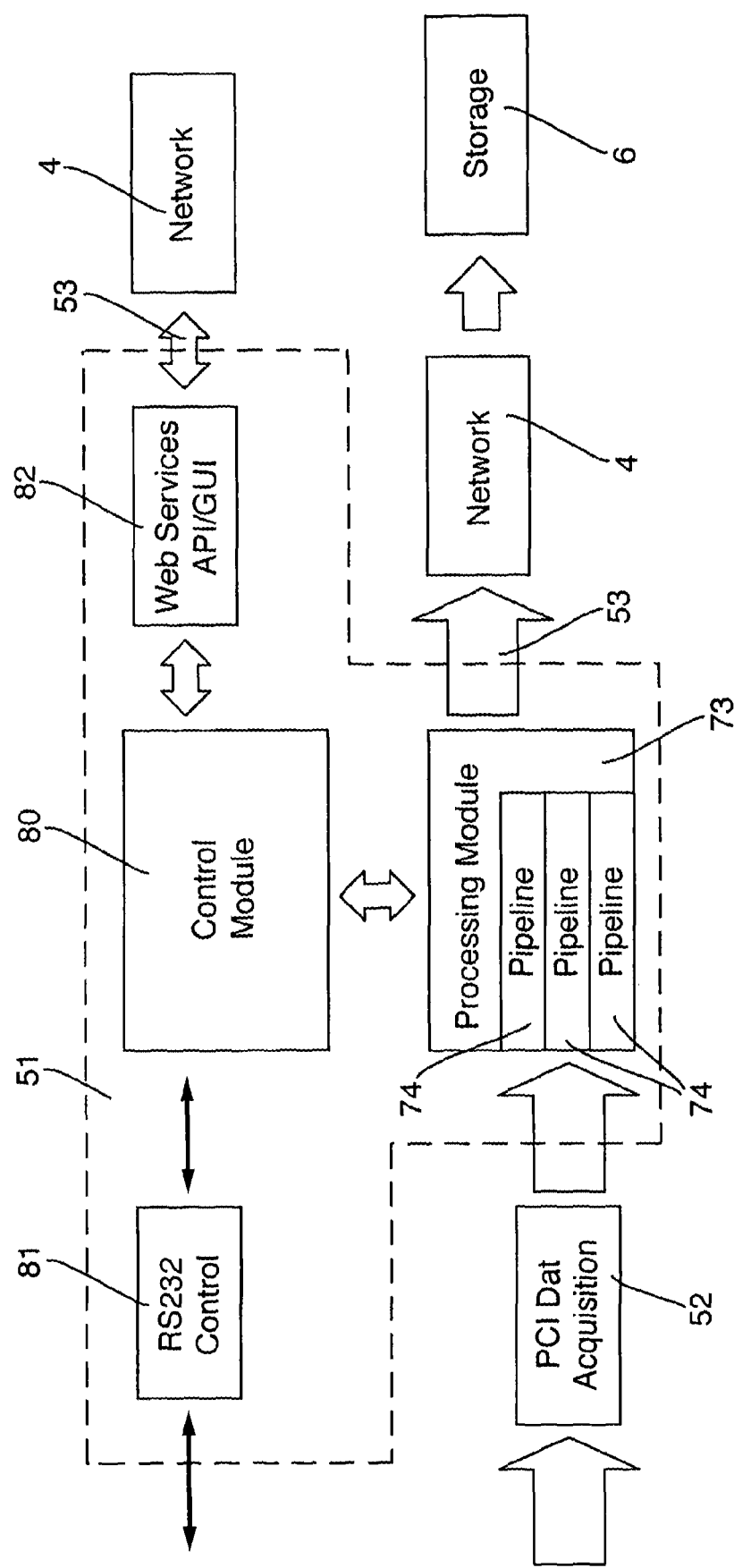

BIOCHEMICAL ANALYSIS INSTRUMENT

RELATED APPLICATIONS

This application is a Continuation of U.S. Ser. No. 14/302,303, filed Jun. 11, 2014, which is a Continuation of U.S. Ser. No. 13/512,937, filed Sep. 6, 2012, which is a 35 U.S.C. 371 National Stage Application of International Application PCT/GB2010/002206, filed Dec. 1, 2010, which claims priority to U.S. Provisional Ser. No. 61/265,488, filed Dec. 1, 2009, in the United States, and United Kingdom Patent Application 0922743.0, filed Dec. 31, 2009, and United Kingdom 1016614.8, filed Oct. 1, 2010, in the United Kingdom. The contents of the aforementioned applications are hereby incorporated by reference.

First and second aspects of the present invention relates to instruments for performing biochemical analysis of a sample, for example sequencing of polynucleotides and/or biochemical analysis using nanopores, which produces output data of plural parallel channels representing the results of the biochemical analysis. The third aspect of the present invention relates to the performance of biochemical analysis of a sample using nanopores, for example sequencing of polynucleotides.

Regarding the first and second aspects of the present invention, there are many types of biochemical analysis that produces output data of plural parallel channels. Instruments for performing such biochemical analysis in an automated manner are known and provide efficiencies in the obtaining of large amounts of output data that are inherent in the biochemical analysis.

Merely by way of example, one such type of biochemical analysis that produces output data of plural parallel channels is DNA sequencing. Conventional DNA sequencing instruments, and laboratory instrumentation in general, are based on a model where an instrument operates as a standalone device. Typically, instruments perform one measurement task in finite time with a pre defined completion criterion. We can describe this design model as "monolithic".

DNA sequencing, as an example, is an inherently high throughput laboratory technique. Experiments cover a wide variety of data sizes and durations and the data produced are very complex, heterogeneous and require intensive downstream processing. The nature of research around DNA sequencing makes it difficult to treat the core of the analysis, the instrument system, as a black box measuring device. There is an increasing need for scalable systems for DNA sequencing, capable of scaling both up and down. This is driven by a recent market demand to sequence more things, different things, and all more cheaply, quickly and effectively. Sequencing systems must therefore also be able to accommodate heterogeneous workflows and be able to pipeline samples of varying types and sizes in accordance with use-cases. This is desirably done efficiently and economically. Measurement artefacts associated with the substrate, or how it has been prepared, should not derail efficient processing on an instrument leading to redundant down-time or wasted reagents. Institutes that can operate efficient factory based sequencing processes will dominate low-cost and high throughput applications. However, these desires are difficult to achieve.

Current monolithic DNA sequencing instruments are difficult to scale to analysis at different scales. The instruments cannot be designed to suit very large factory operations, whilst at the same time being accessible to unskilled laboratory staff with smaller projects. Scalability for current DNA sequencing instruments generally comes from increasing the amount of data they can produce in a run, that is a single analysis performed by one instrument. However, modularity and flexibility is limited and in order to achieve it, the user has to resort to breaking the substrates down, making the substrates individually addressable by adding labels, and by breaking down the reaction chambers of the sequencers. In either case, artefacts are introduced and there are intrinsic limits on how much scale of modularity can be accomplished without a complete redesign of the instrument itself. In other words, the basic design of the instrument has a built in resource limit that hinders it ability to cope with the demands of real world workflows.

In many DNA sequencing instruments, individual strands or clonally amplified colonies of limited lengths of DNA are localised to a surface or to a bead. This surface/bead array is usually in a flow cell that enables reagents to be passed across them thus applying chemistries of various types that allow the DNA to be decoded. The biochemical analysis process within most instruments uses a stepwise cyclical chemistry, followed by an imaging stage to detect the incorporation, annealing or removal of chemically labelled fluorescent probes that enable the DNA under study to be decoded.

During the base identification stages, in most systems a high resolution imaging device takes pictures of the entire flow cell surface as a sequential series of tiled arrays of images. In some technologies, a single region is imaged very quickly detecting chemistry cycles in real time as bases are incorporated asynchronously.

Generally, in the case of sequential imaging of synchronous chemistry based systems, the entire imaging step takes a significant amount of time and generally has to complete a preset number of chemistry cycles, or preset run-time, before the user can take the data and analyse it, thereby judging if the experiment has been successful and yielded enough useful information. Generally, only following the analysis, can the user decide if the experiment has been successful, and if so, then an entirely new analysis run has to be performed, and this repeated until enough data of the required quality has been collected. In most cases each run has a fixed cost derived from the price of reagents. Hence the price of success is difficult to determine upfront as is the time-to-result.

For many instruments one run takes at least several days or often weeks with significant chance of failure by the instrument during the experiment, generally causing truncation or even complete loss of data. Higher outputs per run can be achieved by packing more DNA molecules into the flow-cell, however this tends to increase the time to take the images, depending on the device resolution and speed/sensitivity, with ultimately limited improvement in net throughput. For example, the company Helicos BioSciences market an instrument referred to as the Heliscope that has 600-800M DNA fragments attached to two flow cells, and the company Illumina market an instrument referred to as the Genome Analyser with 80M-100M DNA fragments. By way of comparison, it takes around 6 hours to incorporate and image a new base in every strand on the Heliscope compared to 1-2 hours per base on the Genome Analyser. Thus the two instruments are each best suited to tasks of different scales.

These vendors of such instrumentation have realised that users do not necessarily want a large output of data on one sample as this substantially reduces the modularity, flexibility and utility, and so typically physically divide up the surface area into individually addressable sections (e.g. 8 sub-channels, or 'lanes', on the flowcell for the Genome Analyser, 25 sub-channels per flow cell for the Heliscope, to enable the user to measure more than one sample per flow cell, albeit at concomitantly reduced data output per sample. One such area will still produce at least 250 Mb of DNA sequence, therefore generating a large over-sampling of a sample containing small genomes, for example a typical bacteria at 0.5 Mb would be covered at least 500 times. This example illustrates the inefficient utilisation of the instrumentation and reagents, both in terms of time and cost for the user.

For the user, one further problem experienced with existing instrumentation is that no matter how few fragments/strands of DNA/samples are required to be sequenced, throughput is tied to the cycle time of measuring across the entire flow cell surface. Current instruments have only one processing unit (the camera/flow cell surface) and cannot divide up the task of measuring each sample sufficiently to give the desired output for the user.

A further problem for the user is that he must pay for the time of the processing unit by way of the depreciation of the upfront costs of the instrument, as well as the costs of reagents across the entire surface in order to achieve his result, without knowing upfront if success is guaranteed in a run.

An specific example of a further compounding problem is that bases do not get added evenly during the biochemical analysis process to each available fragment (some fragments will happen to have a disproportionate amount of A's over C's for example, consist of repeating homopolymers), and are not always measured with even accuracy (dephasing of clusters, out-of focus areas on flow cell, enzyme/polymerase breakdown, background signal build up). This means that some areas of the flow cell will generate more data than others, but the nature of the single processing unit means that it cannot adapt to either maximise those areas that are generating useful and high quality information, or focus on areas that are failing to deliver sufficient data.

In summary, existing systems run for defined period of time and therefore cost, but produce information for a fixed number of bases for the user at variable measurement quality. The net result for the user is great inefficiencies in time and cost when performing different DNA sequencing experiments given the range of applications of interest to the user. This is particularly so when the user is trying to analyse, in parallel, multiple samples within a project on a given class of sequencing device.

Although a DNA sequencing instrument has been discussed as an example for illustration, difficulties of a similar nature may be encountered in designing instruments for a wide range of biochemical analysis that produces large amounts of output data of plural parallel channels.

The first and second aspects of the present invention seeks to alleviate some of these problems in scaling an instrument for performing biochemical analysis.

Regarding the third aspect of the present invention, in recent years there has been considerable development of biochemical analysis of a sample using nanopores. A nanopore is a small hole in an electrically insulating layer and may be formed, for example, by protein pores or channels introduced into an amphiphilic membrane. The nanopores may allow a flow of ions to travel across the amphiphilic membrane, modulated by the nanopore on the basis of an analyte interaction, thus allowing the nanopore to provide a biochemical analysis. Various types of nanopore and analysis apparatus for using them have been developed for a range of types of biochemical analysis. One example of commercial interest is to use nanopores for sequencing of polynucleotides such as DNA. One example of an analysis apparatus for performing biochemical analysis of a sample using nanopore is disclosed in WO-2009/077734.

As such nanopores offer the potential of a platform for biochemical analysis on a commercial scale. However, in such a context it would be desirable to provide efficient handling of samples in the apparatus in order to maximise throughput and minimise costs of performing the biochemical analysis.

According to a first aspect of the present invention, there is provided an analysis instrument for performing biochemical analysis, the instrument comprising plural modules, each module comprising an analysis apparatus that is operable to perform biochemical analysis of a sample, the module being arranged to produce output data of at least one channel representing the results of the biochemical analysis, the operation of the module being controllable in a manner that varies its performance, the analysis instrument further comprising a control system that is arranged to accept input selecting an arbitrary number of modules as a cluster for performing a common biochemical analysis and to accept input representing global performance targets in respect of the common biochemical analysis, the control system being arranged to control the operation of the modules of the cluster to perform the common biochemical analysis, and wherein the control system is arranged to determine, at least once during the performance of the common biochemical analysis, measures of performance of each module from the output data produced by the modules, and the control system is arranged (a) to vary the control of the operation of the modules of the cluster on the basis of the determined measures of performance of all the modules and the global performance targets, and/or arranged (b) to take remedial action in response to the global performance targets not being achievable on the basis of the determined measures of performance of all the modules.

Instead of the user having a single instrument, similar to existing monolithic instruments in the case of DNA sequencing, the user has a parallelized group of modules at their disposal and is able to group any number of such modules into larger instrument that can perform a common biochemical analysis. Thus, the instrument is physically parallelised in the sense that it comprises plural modules, each comprising an analysis apparatus that is operable to perform biochemical analysis of a sample. The modules may, but are not required to be, identical. In this way a common biochemical analysis can be performed across an arbitrary number of such modules. This provides scalability in that the number of modules can be selected that is suitable to perform the biochemical analysis that may in general require different amounts of resource depending on its nature. The size and utility of the cluster is a function of the arbitrary number of individual modules that are selected. The design of the modules and the encapsulated functionality allows them to be scaled linearly as a single operating unit with reference to an external controlling system or gateway computer. This scalability provides efficiency gains, because an appropriate number of modules may be selected for the task at hand, thereby freeing up other modules for other tasks.

An arbitrary number of such physical modules can be run, addressed and treated as a single logical device. However the size and utility of the logical device is a function of the arbitrary number of individual modules the user has built into the ensemble (or 'cluster').

Equally importantly, an individual module can be addressed by a user (or software) and operated as a standalone unit, performing the same core tasks as the ensemble but in isolation. No further modification of the modules is required in order to run them individually or in large groups.

Furthermore, efficiency gains are achieved beyond those resulting purely from scalability of the number of modules, because the operation of the individual modules may be also intelligently parallelised. This makes use of the capability for independent control of the analysis apparatuses of each module, as follows. Measures of performance of each module are determined from the output data produced by the modules. These measures of performance are used as the basis to control the operation of the modules to meet global performance targets set by input, e.g. user-input or stored data in respect of the biochemical analysis being performed. Such performance targets and measures may be the time for producing output data, the quantity of output data, and/or the quality of output data. This determination is performed at least once, or preferably repeatedly, or even continuously, during the performance of the common biochemical analysis.

The control of the operation of the analysis apparatus of the individual modules may be varied on the basis of the measures of performance for the cluster of modules to meet the global performance targets. In general the performance of each module can vary on the basis of numerous factors, and so this control of the operation of each module allows the overall performance of the instrument to be managed to meet the global performance targets. This produces efficiency gains, because better use is made of the individual modules in the cluster.

Alternatively or additionally, remedial action may be taken in response to the global performance targets not being achievable. A variety of remedial action is possible, for example increasing the number of modules performing the common biochemical analysis, producing output to notify a user, or even stopping the biochemical analysis. This produces efficiency gains, because better use is made of the individual modules in the cluster. For example, employing additional modules allows the meeting of targets that otherwise would be missed, or stopping the analysis frees up the modules for another biochemical analysis.

By way of example, the instrument can measure the quantity and quality of output data in real time, and provide dynamic flexibility to respond and adapt to the global performance targets set by the user to maximise time and cost efficiencies. Such an instrument could then vary the performance of the biochemical analysis in any of the modules, as necessary. Examples of such parameters that may be controlled include: the temperature of the analysis apparatus; parameters of the biochemical analysis, e.g. electrical, optical; fluidics parameters; or sampling characteristics of the output data. Examples of electrical parameters are bias voltage and current. Examples of fluidics parameters are flow rate, addition of sample, removal of sample, change of buffer, addition or removal of reagents, addition or removal of nanopores, replacement of bilayer and refresh of system. Examples of sampling characteristics are sample rate, amplifier reset time and amplifier settings such as bandwidth, gain, integrator capacitance. Variation of these and other parameters allows the performance to be varied, for example changing the amount, quality and rate of the output data. It is, for example, possible to finish the analysis when sufficient data has been gathered, or to focus on samples within the experiment that have yet to produce enough data, whilst freeing up resources from samples that have already produced sufficient data according to the user's experimental requirements.

For example, in the case that the biochemical analysis is sequencing of a polynucleotide in the sample, the instrument can be operated in numerous different ways, for example: until a defined number of bases have been sequenced; until particular sequence is detected, e.g. pathogen detection amongst large background, cancer mutation detection in plasma DNA; for very long periods of time to enable measurement of very rare amounts of polynucleotide; or providing an analysis pipeline at optimal performance without user guidance.

Such an intelligent and modular sequencing instrument allows radically re-shaping of workflows to provide efficient pipelining of experiments and samples. Workflows can be optimised in terms of priority, time, cost and overall outcome. This gives a significant efficiency gain over traditional monolithic instruments.

Further according to the first aspect of the invention, there may be provided a single module in isolation, that is capable of connection to other modules to form such a biochemical analysis apparatus, or there may be provided a corresponding method of operation of an analysis apparatus.

Advantageously, the modules are capable of connection to a data network to allow connection together over the network, for example on a peer-to-peer basis. This allows the control system to take advantage of the data network to facilitate communication and control.

Although the control system could be implemented in an independent device that is connected to the network, advantageously, the control system comprises a control unit in each module that is operable to control the operation of that module. In this case, the control units may be addressable over the data network to provide said input selecting an arbitrary number of modules to operate as a cluster for performing a common biochemical analysis and to said user-input representing global performance targets in respect of the common biochemical analysis. For example, this may be achieved by the control units being arranged to present a user-interface over the data network for a computer connected thereto, for example using a browser. Then, the control units of the modules of the cluster control the operation of their respective modules to perform the common biochemical analysis.

Such division of the control system into the control units of the modules allows the modules themselves to be addressed and operated as a single instrument, simply on connection of the modules to the network. Large groups of modules can be managed to provide biochemical analysis interfaces of any number of more simply because the network interface allows a single command to simultaneously issue to a cluster. Similarly feedback and data from any cluster of modules can be collated and logically formatted and addressed like the output from a single module. This efficiency of operation may manifest itself as pipelining and may have positive knock on effects on the upstream preparation of samples, and the downstream analysis of output data. Thus the overall workflow of a laboratory, from substrate to analyses, can be made more efficient regardless of how complex or heterogeneous the substrate or analysis has to be. The provision of the control units in the modules also means that an individual module has the capability of being addressed and operated as a stand-alone unit, performing the same core tasks as the cluster but in isolation. Thus, no further modification of the modules is required in order to run them individually or in large groups.

The respective control units of the modules of the cluster may be arranged to derive the measures of performance in respect of their respective module from the output data produced by their respective module, and to communicate the measures of performance over the data network to form the basis of the decision on further control. By deriving the measures of performance locally in the modules, it is only necessary to share the measures of performance for implementing the control. This facilitates the control and reduces bottlenecks in the data flows as the measures of performance require a significantly smaller amount of data than the output data.

The control units of the modules of the cluster may be arranged to communicate over the data network to make a decision on controlling further operation. This has the advantage that the control system is implemented by providing control units in each of the modules. Thus a group of modules may be operated simply by connecting the modules to a data network, without the need for any additional control system to be provided.

Advantageously, the control system is arranged to determine local performance targets for each module on the basis of the global performance targets and the control unit in each module is arranged to control the operation of that module on the basis of its local performance target. In this manner, the control system may vary the local performance targets, on the basis of the determined measures of performance and the global performance targets, in order to vary the control of the operation of the modules of the cluster.

There are numerous ways to distribute the determination of the local performance targets.

In a first implementation, this determination may be performed in all the control units, for example each control unit determining its local performance target. This provides load-sharing of the processing performed by the control units, both to derive the measures of performance and to determine the required operation. This also provides scalability of operation and management by avoiding a single gate-way or bottle-neck computer system.

In a second implementation, this determination may be performed in one (or a subset) of the control units. This concentrates determination of the local performance targets on a single control unit (or a subset of the control units in the cluster), which increases the processing burden on that control unit, but may simplify the processing needed to perform the determination.

In a third implementation, this determination may be performed in a separate federation control unit also connected to the data network. This concentrates the determination of the local performance targets on a separate federation control unit, which decreases the processing burden on the control units of the modules. This is at the expense of requiring an additional federation control unit but there may be advantages in simplifying the processing needed to perform the determination.

The instrument may in general be for performing any type of biochemical analysis, for example analysis of a molecule in a sample, for example a polymer or more specifically a polynucleotide.

In one advantageous example, the biochemical analysis is sequencing of a polynucleotide in the sample, so the output data includes sequence data representing a sequence of the polynucleotide.

In another advantageous example, the analysis apparatus is capable of supporting plural nanopores and is operable to perform biochemical analysis of a sample using the nanopores, for example using electrodes to generate an electrical signal across each nanopore case from which the output data is derived. In this case, the biochemical analysis may again be sequencing of a polynucleotide, but nanopores can equally be used to provide other types of biochemical analysis.

The second aspect of the present invention is specifically concerned with an instrument for performing biochemical analysis of a sample using nanopores where electrodes are used to generate an electrical signal across each nanopore and a signal processing circuit is used to generate output data of plural parallel channels from the electrical signals. This type of instrument is known, for example, from WO-2009/077734. However it remains desirable to optimise the efficiency of the instrument in producing the output data.

According to the second aspect of the present invention, there is provided a module for performing biochemical analysis, the module comprising:

an analysis apparatus that is capable of supporting plural nanopores and being operable to perform biochemical analysis of a sample using the nanopores, the analysis apparatus comprising electrodes arranged to generate an electrical signal across each nanopore; and a signal processing circuit arranged to generate from the electrical signals generated from said electrodes output data of plural parallel channels representing the results of the biochemical analysis, the module being controllable in a manner that varies its performance and further comprising a control unit operable to control the operation of the module on the basis of a performance target.

Such a module provides efficiency gain in the generation of output data from the biochemical analysis because the operation of the module is controlled on the basis of performance targets. Such performance targets and measures may be the time for producing output data, the quantity of output data, and/or the quality of output data.

The control unit may be arranged, at least once during the performance of the biochemical analysis, to determine measures of performance of the biochemical analysis and to vary the control of the operation of the module on the basis of the measures of performance to meet the performance targets. This provides efficiency gain in the generation of output data from the biochemical analysis because the operation of the module is intelligently controlled, as follows. The control unit determines measures of performance from the output data produced by the module and varies the experimental parameters of the biochemical analysis on the basis of the measures of performance to meet performance targets. This determination and control may be performed repeatedly, or even continuously, during the biochemical analysis. Examples of the experimental parameters that may be varied include the temperature of the analysis apparatus, electrical parameters of the biochemical analysis, or sampling characteristics of the output data. Variation of these and other experimental parameters allows the performance to be varied, for example changing the amount, quality and rate of the output data. In general, the performance of the module can vary on the basis of numerous factors, and so this dynamic operational control allows the overall performance of the instrument to be managed effectively to meet the targets. This produces efficiency gains.

For example, in the case that the biochemical analysis is sequencing of a polynucleotide in the sample, the instrument can be operated in numerous different ways, for example: until a defined number of bases have been sequenced; until particular sequence is detected, e.g. pathogen detection amongst large background, cancer mutation detection in plasma DNA; for very long periods of time to enable measurement of very rare amounts of polynucleotide; or providing an analysis pipeline at optimal performance without user guidance.

U.S. Application No. 61/170,729 discloses a method of sensing a physical phenomenon, the method comprising: providing a sensor device comprising an array of sensor elements including respective electrodes, each sensor element being arranged to output an electrical signal at the electrode that is dependent on a physical phenomenon with a performance that is variable; providing a detection circuit comprising a plurality of detection channels each capable of amplifying an electrical signal from one of the sensor elements, the number of sensor elements in the array being greater than the number of detection channels; providing a switch arrangement capable of selectively connecting the detection channels to respective sensor elements; controlling the switching arrangement to selectively connect the detection channels to respective sensor elements that have acceptable performance on the basis of the amplified electrical signals that are output from the detection channels. Optionally, the second aspect of the invention may exclude the method disclosed in US Application No. 61/170,729.

A module in accordance with the second aspect of the invention may optionally be capable of operating as part of a cluster to perform a common biochemical apparatus in accordance with the first aspect of the invention.

The module may in general be for performing any type of biochemical analysis using the nanopores. In one advantageous example, the biochemical analysis is sequencing of a polynucleotide in the sample, so the output data includes sequence data representing a sequence of the polynucleotide.

According to the third aspect of the present invention, there is provided an module for performing biochemical analysis, the module comprising an electronics unit and a cartridge that is removably attachable to the electronics unit, wherein the cartridge comprises:

a sensor device that is capable of supporting plural nanopores and being operable to perform biochemical analysis of a sample using the nanopores, the sensor device comprising an electrode arrangement across each nanopore;

at least one container for receiving a sample;

at least one reservoir for holding material for performing the biochemical analysis; and a fluidics system configured to controllably supply a sample from the at least one container and material from the at least one reservoir to the sensor device, and the electronics unit contains a drive circuit and a signal processing circuit arranged to be connected to the electrode arrangement across each nanopore when the cartridge is attached to the electronics unit, the drive circuit being configured to generate drive signals for performing the biochemical analysis and the signal processing circuit being arranged to generate output data representing the results of the biochemical analysis from electrical signals generated from the electrode arrangement across each nanopore.

The module has a construction that encapsulates the components and material necessary to perform the biochemical analysis in a cartridge separately from the electronics unit including a drive circuit and a signal processing circuit. In particular, the module incorporates the sensor device operable to perform biochemical analysis of a sample using the nanopores with at least one reservoir for holding the necessary material and a fluidics system that may supply the material to the sensor device, under suitable control. The cartridge is removably attachable to the electronics unit, thereby allowing the cartridge to be replaced for performance of an analysis of further samples. This allows for efficient performance of the biochemical analysis.

Embodiments of the present invention will now be described by way of non-limitative example with reference to the accompanying drawings, in which:

FIG. 8 is a schematic diagram of the electrical circuit of a module;

FIG. 9 is a schematic diagram of the control unit;

Figure 1:
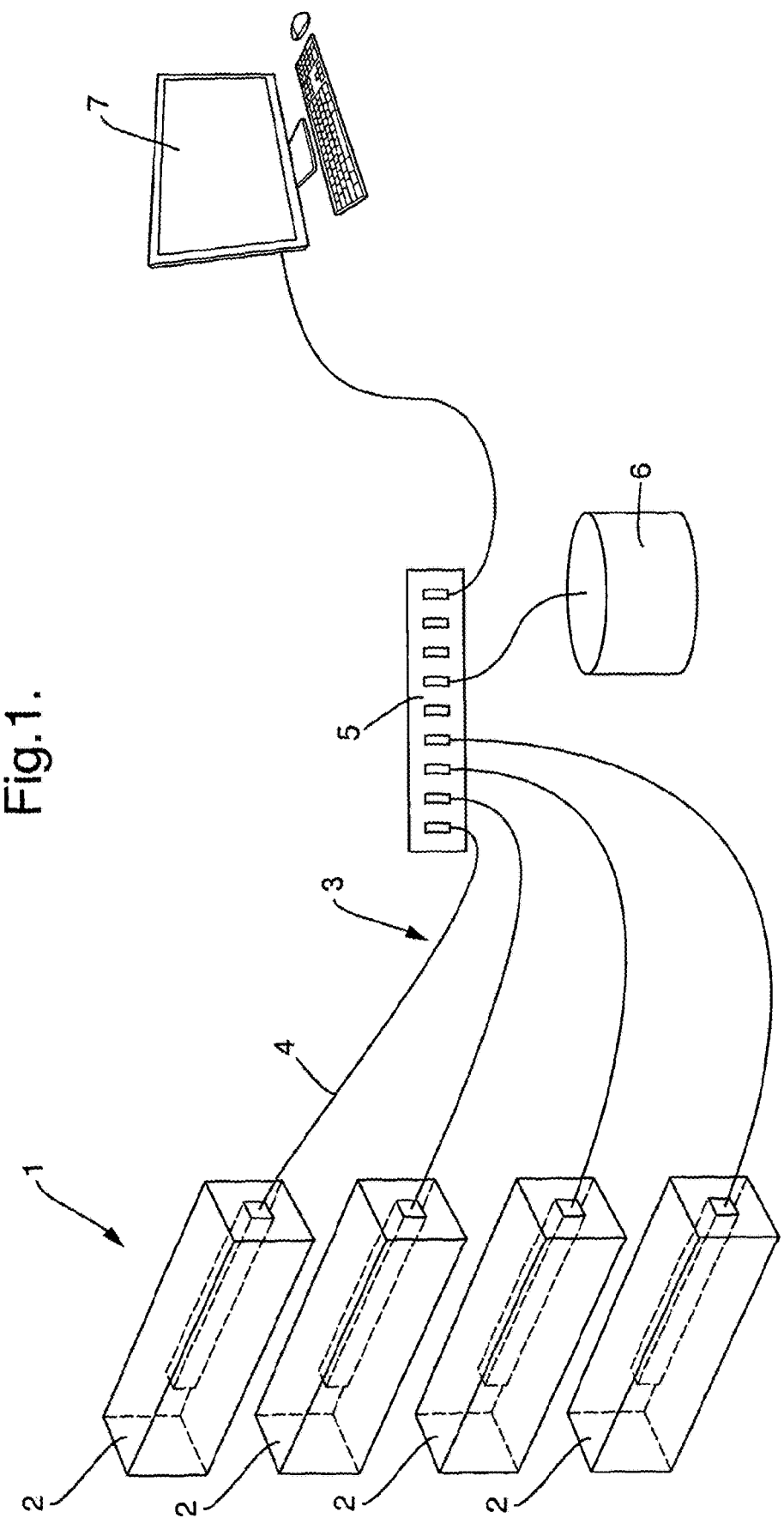
FIG. 1 is a schematic view of a biochemical analysis instrument.

There will first be described an instrument for performing biochemical analysis using nanopores in the form of protein pores supported in an amphiphilic membrane, but this is not limitative of the invention.

The instrument 1 is formed a plurality of modules 2 that are each connected to a data network 3. In this example, the network 3 is formed as a conventional local area network by each module 2 being connected by a cable 4 to a network switch 5. In general, the modules 2 may be connected to any type of data network, including wireless networks, wide-area networks and the internet.

Attached to the network 3, there may also be a storage device 6 of any type, for example a NAS, and an external computer 7 that is used to address the modules 2 and may be a conventional computer having an HTTP browser.

Due to the networked configuration of the instrument 1, any number of modules 2 may be provided in a given location, depending on the local requirements, for example from a small number of modules 2 or even a single module 2 in a small-scale research facility to a large bank of modules 2 in a commercial sequencing centre. Similarly the modules 2 need not be physically close and so the instrument 1 may be formed from modules 2 that are distributed in different locations, even different countries.

An individual module 2 will now be described.

Figure 2:
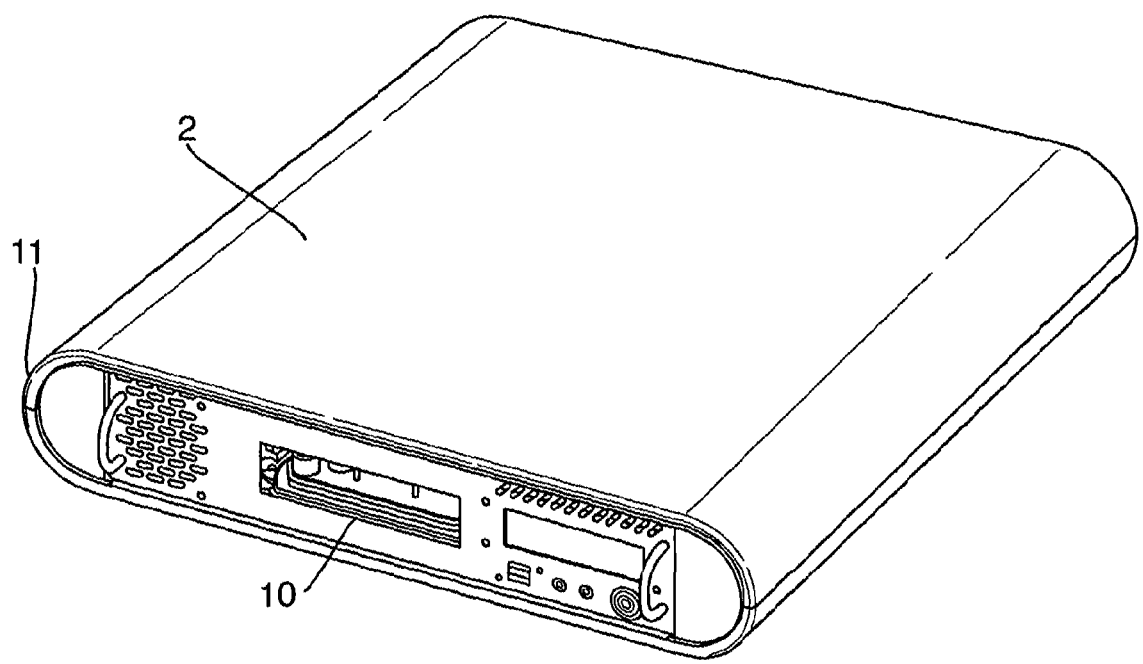
FIG. 2 is a perspective view of a module of the instrument.

As shown in FIG. 2, the module 2 has a cartridge 10 that is replaceable in the housing 11 of the module 2. The cartridge 10 forms an analysis apparatus for performing a biochemical analysis as will now be described. The cartridge 10 has two alternative constructions shown in FIGS. 3 and 10.

Figure 4:
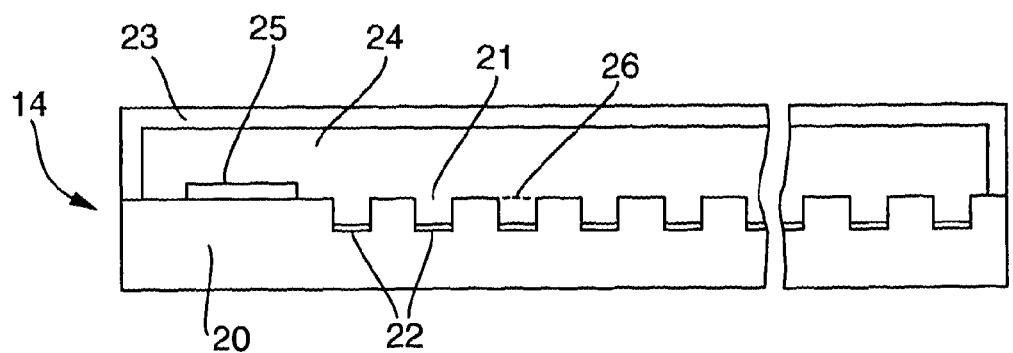
FIG. 4 is a cross-sectional view of a part of a sensor device of the cartridge.

The cartridge 10 comprises a body 37 formed for example of moulded plastic. The body 37 of the cartridge 10 mounts a sensor device 14 that is an apparatus as described in detail in WO-2009/077734 which is incorporated herein by reference. Without limitation to the generality of the teaching therein, the sensor device 14 has a construction as shown in cross-section in FIG. 4 comprising a body 20 in which there is formed a plurality of wells 21 each being a recess having a well electrode 22 arranged therein. A large number of wells 21 is provided to optimise the data collection rate. In general, there may be any number of wells 21, although only a few of the wells 21 are shown in FIG. 4. In one example, the number of wells is 256 or 1024, but there could be one, two or three orders of magnitude more. The body 20 is covered by a cover 23 that extends over the body 20 and is hollow to define a chamber 24 into which each of the wells 21 opens. A common electrode 25 is disposed within the chamber 23.

The sensor device 14 is prepared to form an amphiphilic membrane 26, such as a lipid bilayer, across each well 21 and to insert nanopores that are protein pores into the amphiphilic membrane 26. This preparation is achieved using the techniques and materials described in detail in WO-2009/077734, but may be summarised as follows. Aqueous solution is introduced into the chamber 24 to form the amphiphilic membrane 26 across each well 21 separating aqueous solution in the well 21 from the remaining volume of aqueous solution in the chamber 24. Protein pores are provided into the aqueous solution, for example by being introduced into the aqueous solution before or after that is introduced into the chamber 24 or by being deposited on an internal surface of the chamber 24. The protein pores spontaneously insert from the aqueous solution into the amphiphilic membranes 26.

A protein pore is an example of a nanopore and may be used to perform a biochemical analysis, as follows. In respect of any given well 21, when a amphiphilic membrane 26 has been formed and a protein pore is inserted therein, the well 21 is capable of being used as a sensor element to sense interactions between molecular entities and the protein pore that are stochastic physical events because the output electrical signal across the amphiphilic membrane 26 is dependent on those interactions in that the interactions cause characteristic changes therein. For example, there will typically be interactions between the protein pore and a particular molecular entity (analyte) that modulate the flow of ions through the pore, creating a characteristic change in current flow through the pore. The molecular entity may be a molecule or part of a molecule, for example a DNA base. Thus the interaction appears as a characteristic event in the electrical signal across the protein pore in each amphiphilic membrane 26.

More details on the nature of the sensor device 14 and the biochemical analysis performed thereby are set out below towards the end of this description.

The electrical signals may be detected as the signals between the well electrodes 22 and the common electrode 25, and may subsequently be analysed to produce output data representing the results of the biochemical analysis. Separate electrical signals are derived from the protein pores in the amphiphilic membranes 26 in different wells 21, each resulting in a different channel of the output data.

A wide range of types of biochemical analysis may be performed. One such biochemical analysis is sequencing of polynucleotides. In this case, the electrical signal is modulated differently for each different base, allowing discrimination thereof.

The body 37 of the cartridge 10 encapsulates the components and material necessary to perform the biochemical analysis and is capable of preparing the sensor device 14 automatically. For this purpose, the cartridge 10 mounts reservoirs 30 containing sufficient volumes the necessary materials, such as buffer solutions, lipids, protein pores (in solution), pre-treatment (if required), and sample, such that many 'refreshes' of the analysis apparatus are possible. Thus the cartridge 10 is fully self-contained in that all reagents and other materials required for the biochemical analysis are present and may be used for sample preparation. The cartridge 10 mounts a waste reservoir 35 for disposal of waste products from the sensor device 14, the waste reservoir 35 being shown in FIG. 11 but beneath the body 37 in the construction of FIG. 3 and hence not visible in FIG. 3.

The body 37 of the cartridge 10 also mounts a fluidics system 31 for supplying the fluids from the reservoirs 30 to the sensor device 14. The fluidics system 31 includes supply channels 32 and inlet pumps 33 for pumping fluids from the reservoirs 30 to the sensor device 14. The fluidics system 31 also includes an output pump 34 for pumping fluids out of the sensor device 14 through an outlet channel 36 connected to the waste reservoir 35 for disposal of the fluids. The pumps 33 and 34 may be syringe pumps depending on volume and flow rate required (for example as supplied by Hamilton Company, Via Crusch 8, Bonaduz, GR, Switzerland CH-7402).

The fluidics system also includes a selector valve 45 disposed in the supply channels 32 between the inlet pumps 33 connected to the reservoirs 30 and the output pump 34. The selector valve 45 selectively connects the sensor device 14 to the reservoirs 30 or to the waste reservoir 35. The waste reservoir 35 is open to atmosphere.

One of the reservoirs 30 holds the lipid and the fluidics system 31 supplies the lipid to the sensor device 14 in the same manner as the other materials. As an alternative for supplying the lipid, the supply channels 32 of the fluidics system 31 may pass into the sensor device 14 through a lipid assembly holding lipid so that the fluid flowing into the sensor device 14 acquires lipid and introduces it into the sensor device 14.

The pumps 33 and 34 may thus be operated to control the flow of fluids to prepare the sensor device 14 to form an amphiphilic membrane 26 across each well 21 and to insert nanopores that are protein pores into the amphiphilic membrane 26, as discussed above.

Figure 3:
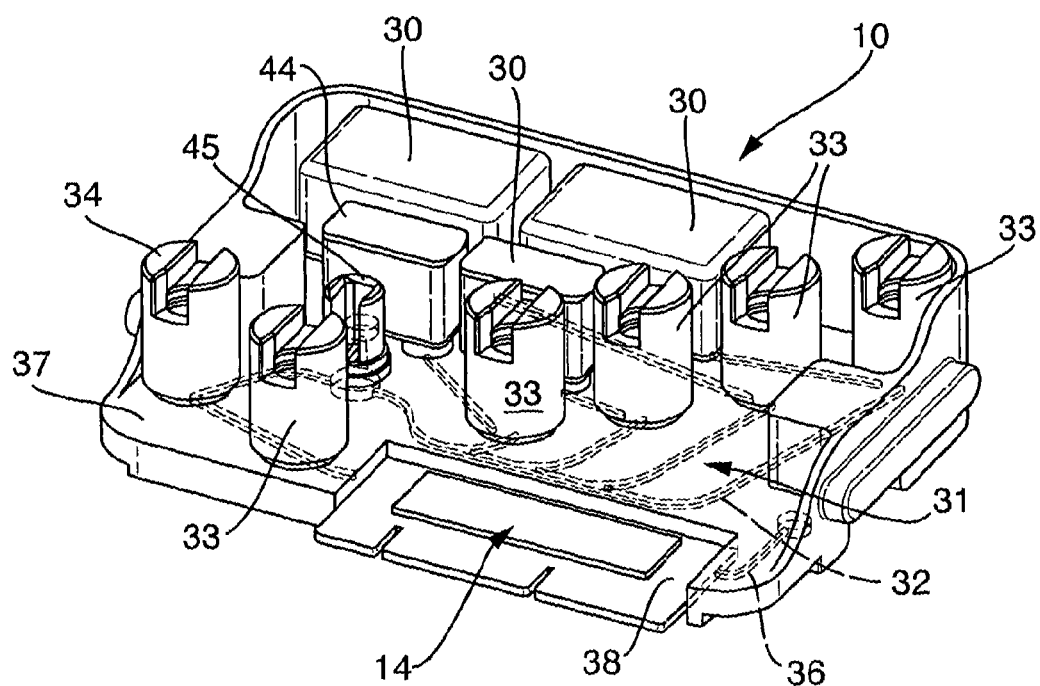
FIG. 3 is a perspective view of a cartridge that is replaceable in the module.

In the construction of FIG. 3, the body 37 of the cartridge 10 mounts a container 44 for receiving a sample. In use, the sample is introduced into the container 44 before loading of the cartridge 10 into the module 2. After preparation of the sensor device 14, the fluidics system 31 is controlled to supply the sample from the container 44 to the sensor device 14 to perform the biochemical analysis.

Figure 11:
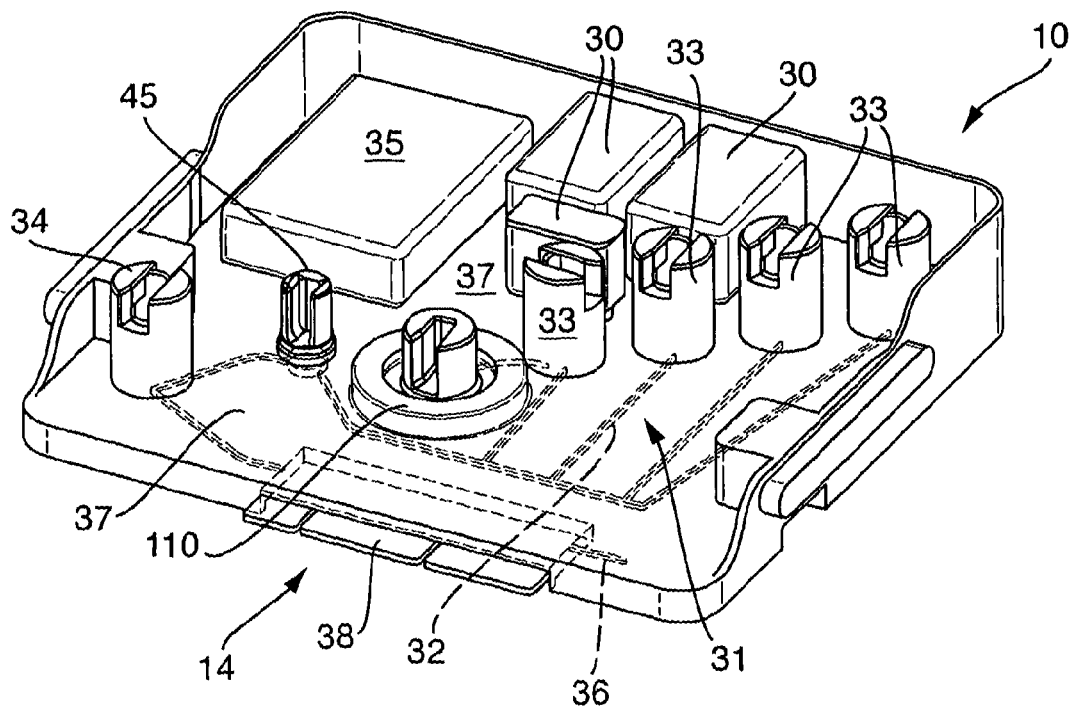
FIG. 11 is a perspective view from above of a cartridge having an alternative construction.
Figure 12:
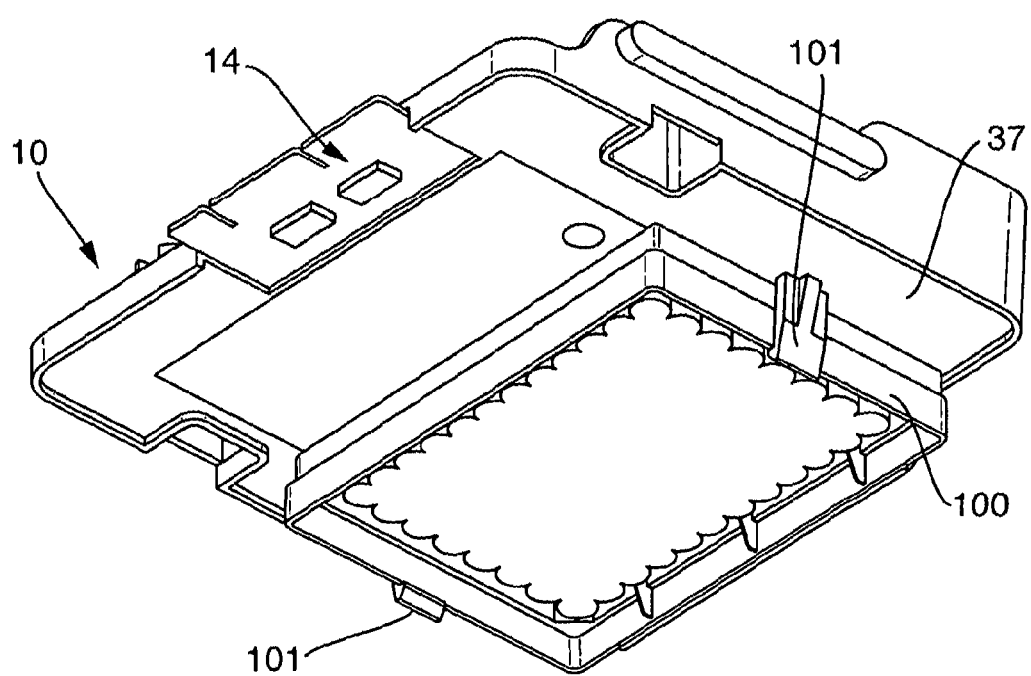
FIGS. 12 and 13 are perspective views from below of the cartridge of FIG. 11, showing a well plate, respectively, attached and separated.
Figure 13:
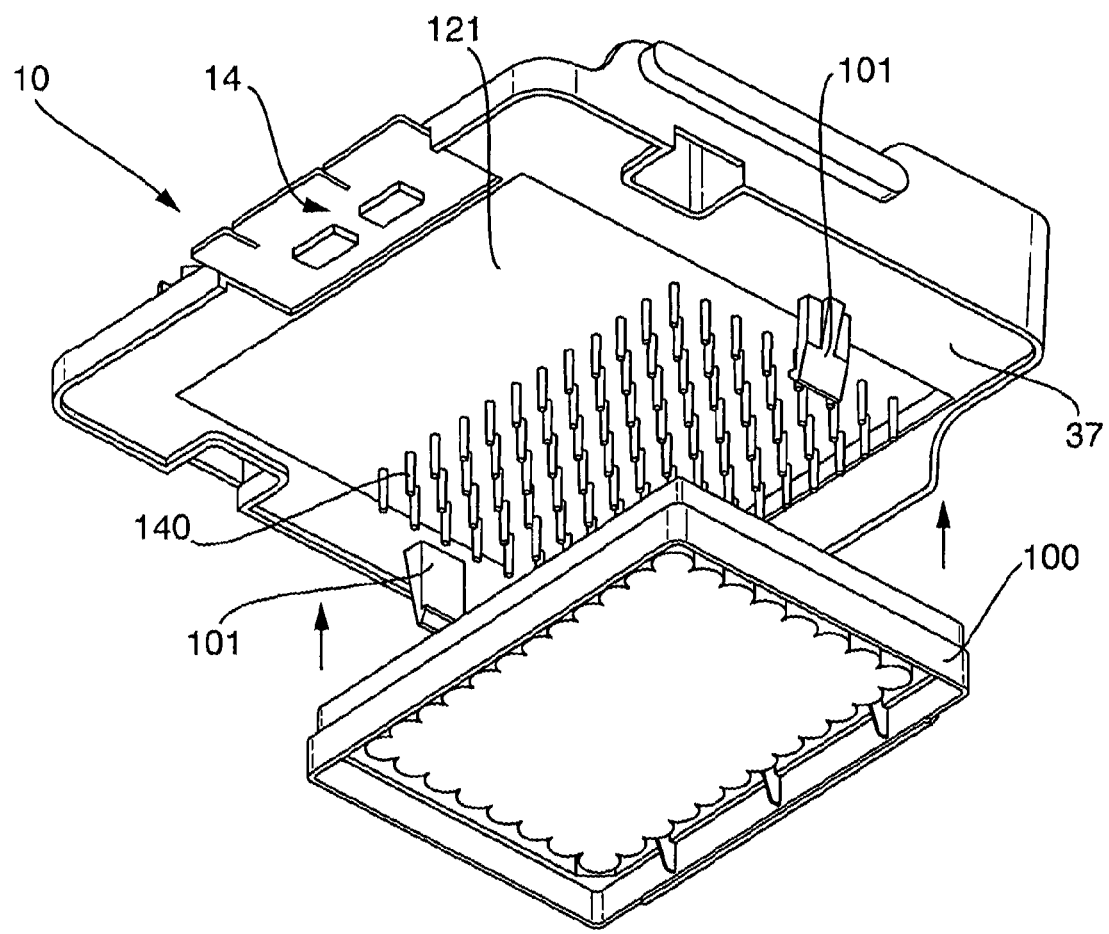

In the construction of FIG. 11, the cartridge 10 is capable of receiving a plurality of samples as follows. As shown in FIG. 12, the body 37 of the cartridge 10 is arranged to allow attachment of a well plate 100. In particular, the body 37 has a pair of clips 101 protruding from its underside and to which a well plate 100 may by attached by pressing the well plate 100 against the clips 101 in the direction of the arrows in FIG. 13.

Figure 14:
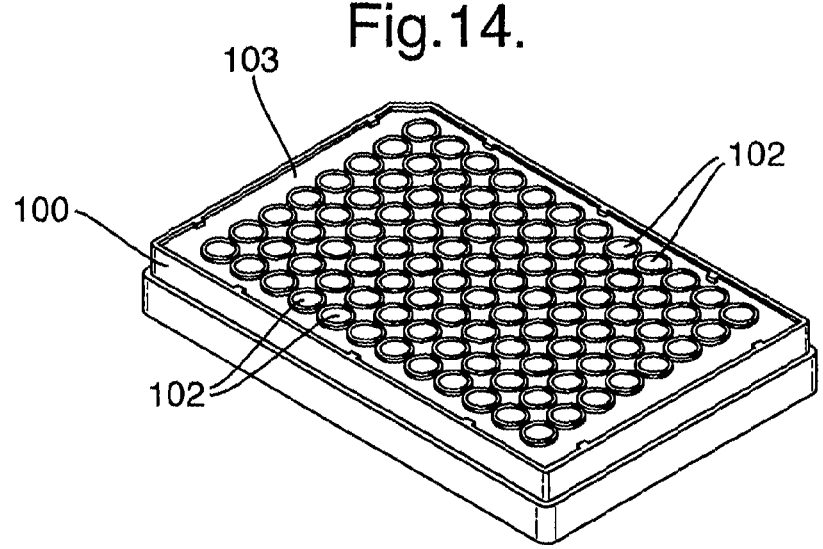
FIG. 14 is a sectioned perspective view of part of the well plate.
Figure 15:
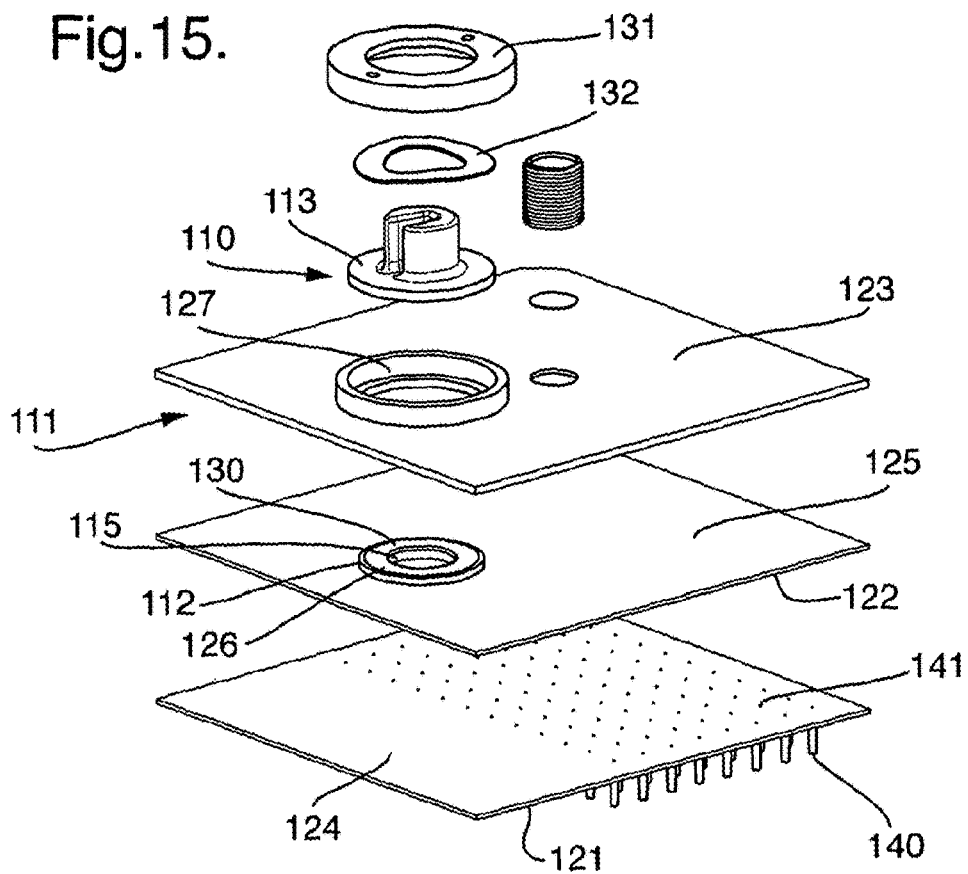
FIGS. 15 and 16 are perspective views from above and below respectively of a valve assembly incorporating a valve.
Figure 16:
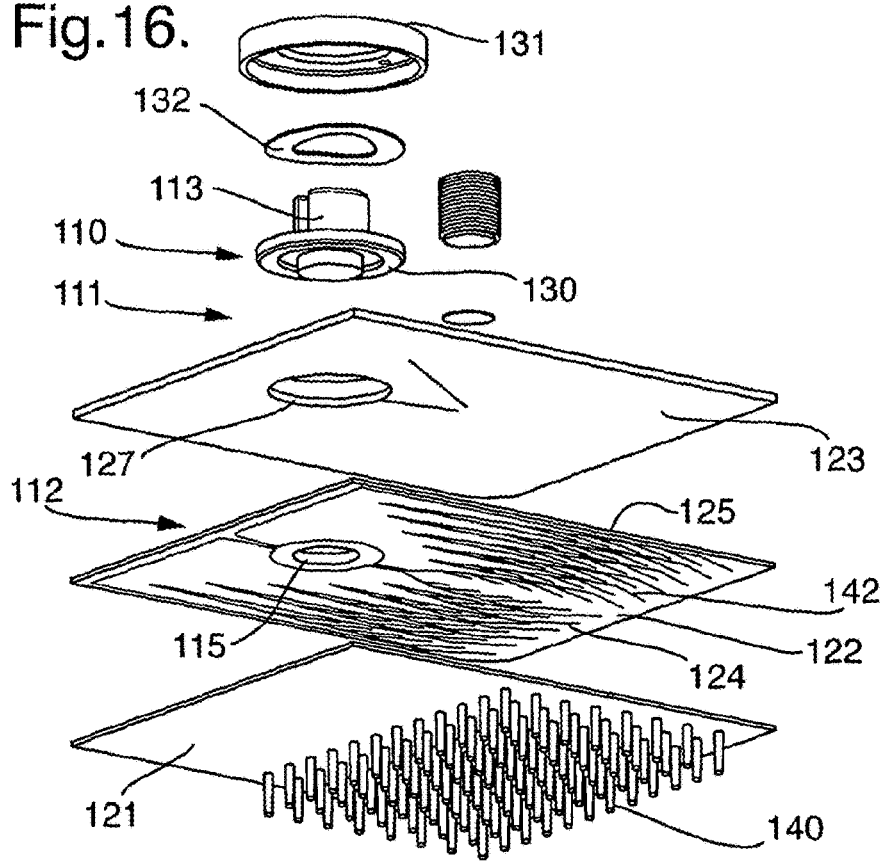

As shown in FIG. 14, the well plate 100 is of standard construction and forms a plurality of wells 102 opening a flat upper surface 103 of the well plate 100. In this example the well plate 100 has 96 wells 102, but in general may have any number of wells 102. The wells 102 are used as containers for receiving respective samples. In use, the samples are introduced into the respective wells 102 before attachment of the well plate 102 to the cartridge 10 and before loading of the cartridge 10 into the module 2. The well plate 102 may be filled with samples using known plate-based parallel manipulation techniques that are intrinsically efficient. As the well plate 100 is a separate element from the body 37 of the cartridge 10 it is easily filled prior to attachment facilitates the filling of the wells 102. More generally, similar advantages could be achieved by replacing the well plate 100 by any other type of container element comprising a plurality of containers that might be wells or closed containers.

After introduction of the samples, the well plate 100 is attached to the cartridge 10 with the flat upper surface 103 against the body 37, to encapsulate the well plate 100 into the cartridge 10. Subsequently, the cartridge 10 is loaded into the module 2.

The fluidics system 31 is configured to supply the samples selectively from the wells 102 to the sensor device 14, using a valve 110 that is a rotary valve and will now be described.

The valve 110 is formed in a valve assembly 111 illustrated in FIGS. 15 to 21 that is incorporated into the body 37 of the cartridge 10.

The valve 110 comprises a stator 112 and a rotor 113. The stator 112 is provided on a body 120 formed by a first plate 121, a second plate 122 and a third plate 123 that are fixed together by interfacing contact surfaces 124 between the first and second plates 121 and 122 and by interfacing contact surfaces 125 between the first and second plates 122 and 123.

The rotor 113 is rotatably mounted on the stator 112 for rotation about a rotational axis R. A bearing for the rotational mounting is provided by the rotor 113 comprising a bearing stub 114 that is mounted in a bearing recess 115 formed in the stator 112. In particular, the bearing stub 114 is has a length chosen to provide a clearance between the end of the bearing stub 114 and the first sheet 121. Around the bearing recess 115, the second sheet 122 has an annular boss 126 that protrudes towards the first sheet 121 and the stator 113, the second sheet 123 having a circular aperture 127 in which the annular boss 126 fits.

In addition the bearing for the rotational mounting is provided by the rotor 113 comprising a disc 116 having a cylindrical outer surface 117 that is mounted in an annular wall 118 formed in the stator 112 and protruding therefrom, in particular from the third plate 123 outside the circular aperture 127. Alternatively, there may be a clearance gap between the disc 116 and the annular wall 118.

The stator 112 and rotor 113 have interfacing contact surfaces 130 that are annular and extend perpendicular to the rotational axis R, being provided as follows. The contact surface 130 of the rotor 113 is formed by a lower surface of the disc 116 that extends perpendicular to the rotational axis R both overlapping the annular boss 126 of the second plate 122 and overlapping the third plate 123 outside the aperture 127. Thus the contact surface 130 of the stator 112 is formed by the adjacent parts of the upper surface of the annular boss 126 of the second plate 122 and the upper surface of the third plate 123, which are flush with each other.

Sealing of the interfacing contact surfaces 130 of the stator 112 and the rotor 113 is facilitated by applying a load between the stator 112 and the rotor 113 along the rotational axis R. This is achieved by a biasing arrangement arranged as follows to bias the rotor 113 against the stator 112. A clamping ring 131 is attached to the stator 113, in particular screwed to the annular wall 118. A disc spring 132 is disposed between and engages the clamping ring 131 and the rotor 112. The disc spring 132 provides resilient biasing between the stator 112 and the rotor 113, although could be replaced by another type of resilient biasing element.

Figure 18:
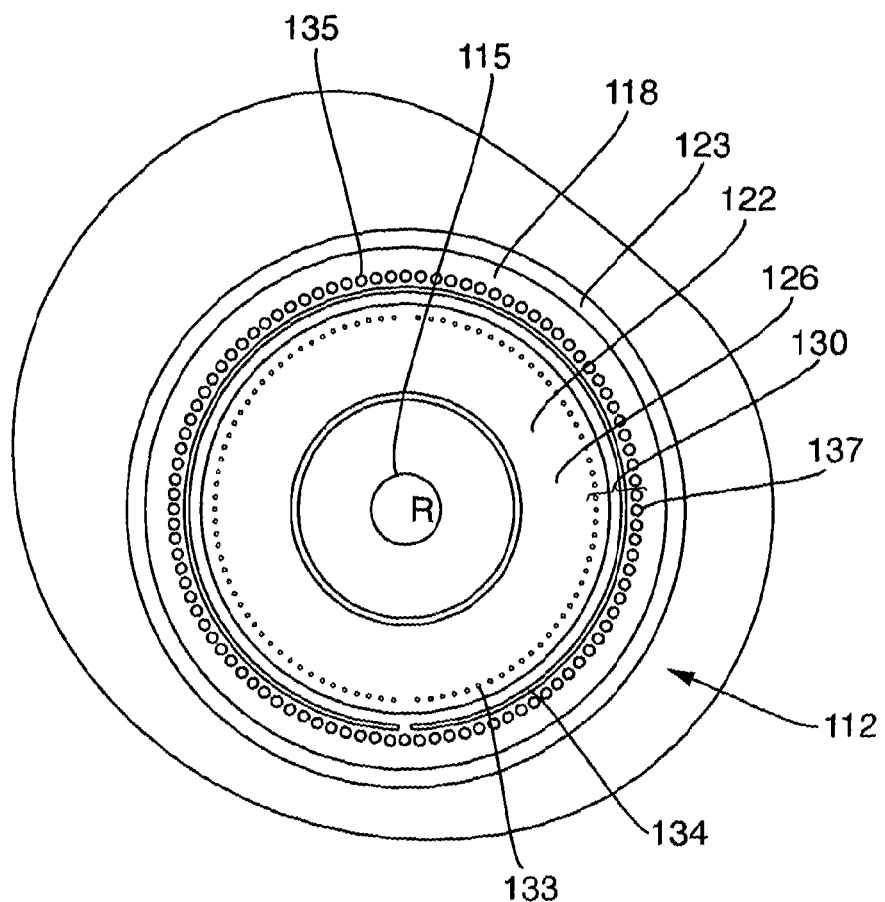
FIG. 18 is a partial plan view from above of a body of the valve assembly around a stator of the valve.
Figure 19:
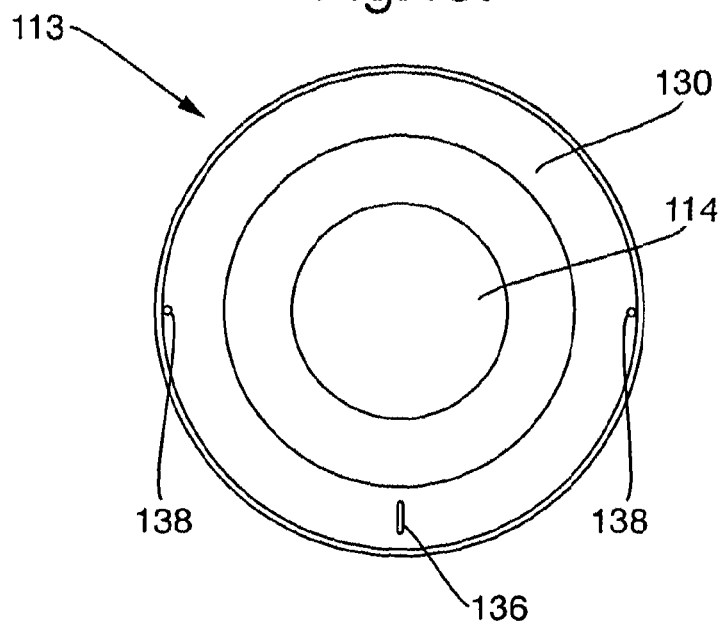
FIG. 19 is a plan view from below of a rotor of the valve.

The contact surface 130 of the stator 112 is arranged as shown in FIG. 18 which is a plan view of the stator 112 without the clamping ring 131. In particular, a plurality of inlet ports 133 are formed in the contact surface 130 of the stator 112 arranged in a circle around the rotational axis R. The inlet ports 133 are evenly spaced, except for a gap at one position, lowermost in FIG. 18. The inlet ports 133 are formed in particular in the upper surface of the annular boss 126 of the second plate 122, facing the contact surface 130 of the rotor 113.

Also, a collection chamber 134 is formed in the contact surface 130 of the stator 112. The collection chamber 134 is formed as a groove in the upper surface of the third plate 122, facing the contact surface 130 of the rotor 113. The collection chamber 134 extends outside the inlet ports 133 in a circular annulus around the rotational axis R aligned angularly with the inlet ports 133, that is with a gap aligned angularly around the rotational axis R with the gap in the inlet ports 133.

The stator 112 further includes an outlet port 135 in communication with the collection chamber 134 by being formed in the lower surface of the collection chamber 134.

The rotor 113 is provided with a passage 136 formed as a groove in the contact surface 130 of the rotor 113. The passage 136 extends radially from the position of the inlet ports 133 to the position of the collection chamber 135. Thus, the passage 136 is capable of communication with any one of the inlet ports 133 depending on the rotational position of the rotor 113. Rotation of the rotor 113 allows different inlet ports 133 to be selected. As the collection chamber 134 is aligned angularly with the inlet ports 133, at all rotational positions where the passage 136 communicates with an inlet port 133, the passage 136 also communicates with the collection chamber 134, thereby connecting the selected inlet port 133 to the outlet port 135. Therefore, rotation of the rotor 136 selectively connects individual inlet ports 133 to the outlet port 135.

When the rotor 133 is aligned with the gap in the inlet ports 133 and the gap in the collection chamber 134, the passage 136 is closed against the contact surface 130 of the stator 112, thereby closing the valve 110. However, as an alternative, the inlet ports 133 can be brought together to omit the gap so that inlet ports are arranged in a complete annulus and the valve 110 cannot be closed.

As an alternative to forming the collection chamber 134 in the contact surface 130 of the stator 112, a similar operation could be achieved by alternatively forming the collection chamber 134 as a groove in the contact surface 130 of the rotor 113 opening into the passage 136.

To provide positioning of the rotor 112, the contact surface 130 of the stator 112 has a circular array of pits 137 at the same pitch as the inlet ports 133, and the contact surface 130 of the rotor 113 has pips 138 that fit into the pits 137. The pips 138 may be pushed out of the pits 137 on rotation of the rotor 112 but are aligned to hold the rotational position of the rotor 112 in stepped rotational positions that each locate the passage 136 in communication with each a respective inlet port 133, or in one of the stepped rotational positions to locate the passage 136 over the gap in the inlet ports 133 and the gap in the collection chamber 134.

The size of the valve 110 is minimised by arranging the inlet ports 133 as close together as possible, but the same operation could be achieved by increasing the size of the gap in the inlet ports 133 so that the inlet ports 133 extend around a smaller part of the annulus. In this case, the collection chamber 134 can be correspondingly reduced in length to extend in a shorter part of the annulus.

The body 120 defines channels connecting the wells 102 of the well plate 100 to the inlet ports 133 as follows.

Figure 20:
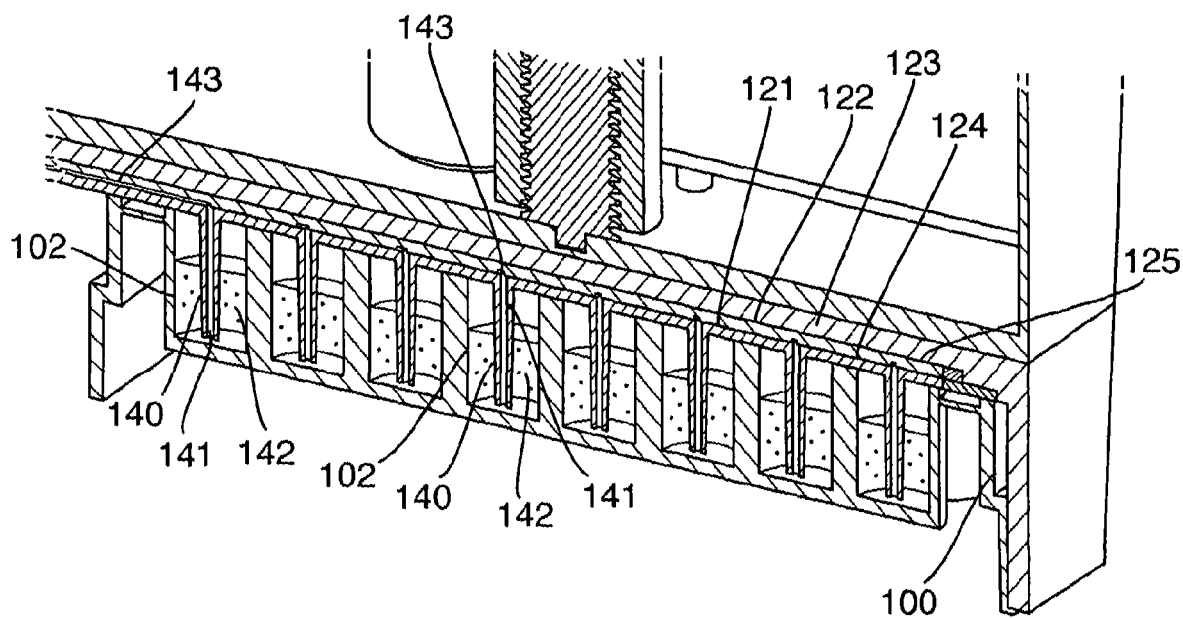
FIG. 20 is a partial cross-sectional view of the body of the valve assembly and a well of the well plate.
Figure 21:
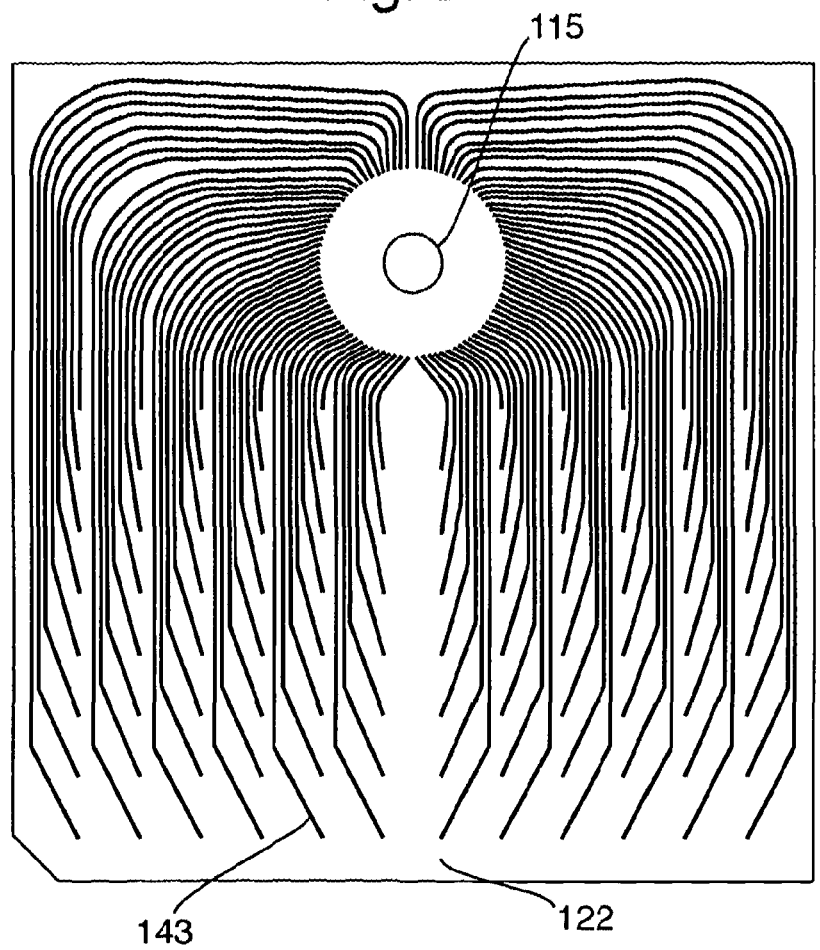
FIG. 21 is a plan view from below of a second plate of the valve assembly.

The first plate 121 is disposed on the underside of the cartridge 10 at the position where the well plate 100 is attached and has an array of nozzles 140 protruding outwardly and having the same spacing as the wells 102 of the well plate 100 to align therewith. As a result, when the plate 100 is attached to the cartridge 10, each nozzle 140 protrudes into a respective well, as shown in FIG. 20. Each nozzle 140 comprises a through hole 141 that extends through the nozzle 140 and through the first plate 121 to the contact surface 124 of the first plate 121 to form part of a channel in respect of the well 102.

The nozzles 140 extend into the wells 102 by a sufficient distance that the end of the nozzle 140 is submerged below the surface of a sample 142 in the well 102. In this manner, the sample 142 effectively seals the nozzle 140. This avoids the need for a hermetic seal between the well plate 100 and the first plate 121.

The contact surface 124 of the second plate 122 is formed with a set of grooves 143 that form part of the channel in respect of each well 102. Each groove 143 communicates at one end with the through hole 141 that extends through the nozzle 140 and through the first plate 121. As shown in FIG. 20, the grooves 143 extend from the nozzles 140 to the stator 112, in particular to the annular boss 126 on the opposite side of the second plate 122 from the outlet ports 133. The remainder of the channels are formed by through holes 144 extending through the boss 126 of the second plate 122 from a respective groove 144 in the contact surface 124 of the second plate 122 to a respective inlet port 133.

Figure 17:
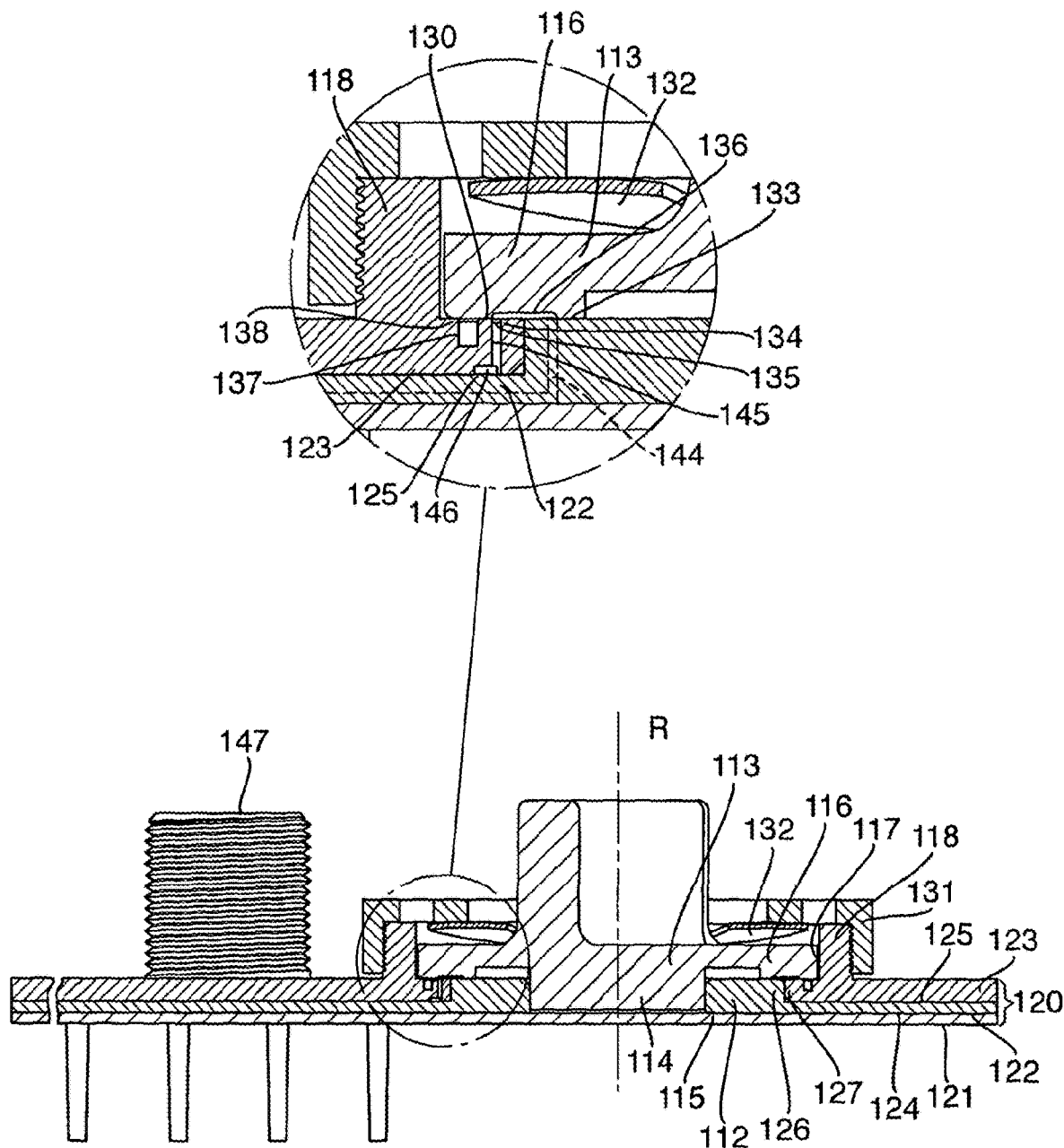
FIG. 17 is a cross-sectional view through the valve assembly.

The body 120 also defines a channel connecting to the outlet port 135 as follows. The third plate 123 has a through hole 145, shown in dotted outline in FIG. 17, that extends from the outlet port 135 through the third plate 123 to the contact surface 125 of the third plate 123, forming part of the channel. The remainder of the channel is formed by a groove 146 in the contact surface 125 of the third plate 123 extending away from the through hole 145. As shown in FIG. 17, the groove 146 extends to a dosing pump 147 operable to pump a sample from a well 102 selected by the rotational position of the valve 110 through the valve 110 to the sensor device 14.

The first, second and third plates 121-123 may be formed from any suitable material that provides sealing for channels defined between the contact surfaces 124 and 125. Suitable materials include PMMA (poly(methyl methacrylate)), PC (polycarbonate) or COC (cyclic olefin co-polymer). The first, second and third plates 121-123 may be sealed by any suitable technique for example ultrasonic welding, laser welding or bonding. PMMA is particularly effective due to the ability to use PMMA diffusion bonds. The first, second and third plates 121-123 may be injection moulded.

Similarly, the rotor 113 may be formed from any suitable material that provides sealing and sufficiently low friction for rotation. One suitable material is PTFE (polytetrafluoroethylene) that may be machined with a section made of an elastomer (e.g. silicone) to provide compression. PTFE can lower the torque required for rotation and has good sealing properties. The elastomer allows the rotor 112 to be clamped but still rotate. Alternatively the rotor 113 can be made from a material that can be injection moulded, for example, FEP (fluorinated ethylene propylene) or UHMWPE (ultra-high-molecular-weight polyethylene).

The valve 110 is not limited to use in the cartridge 10 and can be used in other applications. The valve 110 may be used for flow in the opposite direction to the inlet ports 133 from outlet port 135 so more generally the inlet ports 133 may be referred to as first ports and the outlet port 135 may be referred to as a second port. The valve 110 is particularly suited as a miniature element for handling low volumes of fluid, in which the inlet ports 133, the passage 136, the collection chamber 134 and the outlet port 135 have cross-sectional areas of no more than 10 mm$^2$, preferably no more than 1 mm$^2$.

Figure 22:
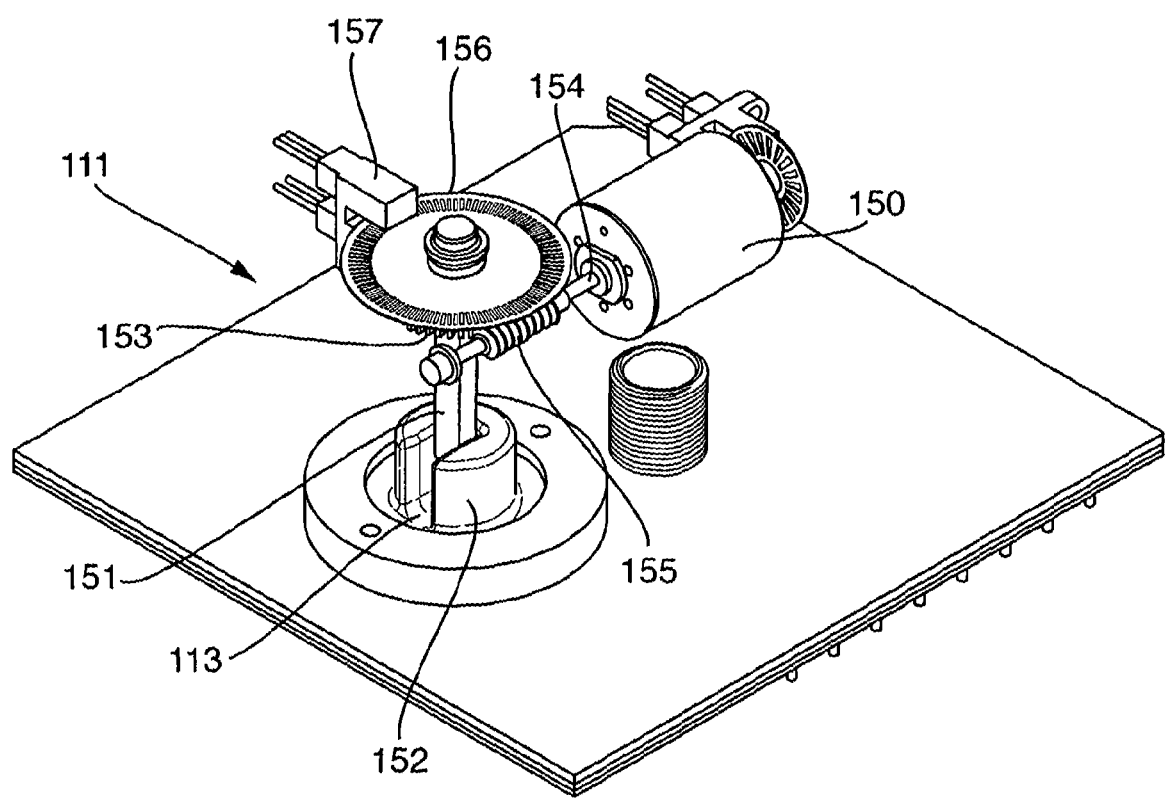
FIG. 22 is a perspective view of the valve assembly including a motor.

The rotor 113 is actuated by a motor 150 as shown in FIG. 22. The rotor 113 has a coupling element 152 protruding upwardly from the rotor 113 and into which is fitted a drive shaft 151 that mounts a gear wheel 153. The motor 151 has an output shaft 154 that mounts a gear profile 155 engaging the gear wheel 153 so that the motor 150 drives rotation of the drive shaft 151 and hence the rotor 113. The drive shaft 151 also mounts an encoder wheel 156 whose position is sensed by a sensor 157. The motor 150 is driven based on the output of the sensor 157, allowing the rotor 113 to be rotated around to select the desired inlet port 133.

The fluidics system 31 is controlled to perform the biochemical analysis in respect of successive samples sequentially. The sensor device 14 is prepared and then the fluidics system 31 is controlled to supply the sample from one of the wells 102 to the sensor device 14. After the biochemical analysis has been performed, the sensor device 14 is emptied and flushed to clear the sample. Then the sensor device 14 is prepared again and the fluidics system 31 is controlled to supply the sample from the next well 102 by rotating the rotor 112 of the valve 110.

A specific example of the method of using the cartridge 10 with the construction of FIG. 11 will now be described. The materials used are those described in detail in WO-2009/077734.

First, a pre-treatment coating is applied to modify the surface of the body 20 of the sensor device 14 surrounding the wells 21 to increase its affinity to the amphiphilic molecules. The required volume pre-treatment is a hydrophobic fluid, typically an organic substance, in an organic solvent is drawn from a reservoir 30 and dispensed by an inlet pump 33 by means of the supply channels 32 to fill the chamber 24 covering the body 20 and the wells 21. The excess material is expelled into the waste reservoir 35.

The cartridge 10 may be used in various configurations to expel the excess pre-treatment. One example is to apply a gas flow with an inlet pump 33 through the supply channels 32 and chamber 24 to move the fluid through the outlet channel 36 into the waste reservoir 35. Alternatively, the pre-treatment may be dispensed from the inlet pump 33 with gas behind the required volume and the excess expelled through the chamber 24 into the outlet channel 36 into the waste reservoir 35 in a single action. The gas flow is continued through the chamber 24 to flush solvent vapour from the system until the final pre-treatment coating is achieved. In further modification, this final step may be achieve more rapidly by warming the gas flow or the body 20.

After application of the pre-treatment coating an aqueous solution, containing amphiphilic molecules, is flowed across the body 20 to cover the wells 21. The required volume of aqueous solution is drawn from the appropriate reservoir 30 and dispensed by an inlet pump 33 by means of the supply channels 32 to fill the chamber 24 covering the body 20 and the wells 21.

Formation of the amphiphilic membrane 26 is formed with the amphiphilic molecules either directly or improved if a multi-pass technique is applied in which aqueous solution covers and uncovers the recess wells 21 at least once before covering the wells 21 for a final time. The aqueous solution containing amphiphilic molecules may be drawn directly from a reservoir 30 or in the alternative approach mentioned above formed by passing aqueous solution through the lipid assembly in the flow path of the supply channel 32 to the chamber 24.

In a first example, multiple passes of the solution air interface can be achieve by reversal of the flow in the chamber 24. The flow to and from the reservoirs 30 is prevented by operation of the selector valve 45 and operation of the output pump 34 drawing the amphiphilic molecule containing solution through the supply channels 32 from the chamber 24 and pulling air from the outlet channel 36 to the waste reservoir 35. The direction of the outlet pump 34 is reversed and solution returned across the solution filled wells 21.

The formation of the amphiphilic membrane 26 may be observed by monitoring of the resultant electrical signals across the electrodes 22 and 25 when a potential is applied the formation introducing a resistive barrier and a decreases in the measured current. In the event that an amphiphilic membrane 26 fails to form, it is a simple matter to perform another pass of the aqueous solution air interface.

Alternatively, in a second example, multiple passes of solution air interface can be achieved by flow in a single direction by inclusion of air slugs in the solution supply. In this second example, the aqueous solution containing amphiphilic molecules is drawn into an inlet pump 33 from the reservoir 30 and then with operation of non-return valves pumped into the supply channels 32. An air slug may be formed by stopping the amphiphilic molecule aqueous solution flow altering the position of the selector valve 45 and required air volume into the channel behind the solution from the waste reservoir 35 (as it is open to atmosphere) by action of another inlet pump 33. The selector valve 45 is returned to the previous position and further amphiphilic molecule aqueous solution pumped forward. As the inlet pump 33 moves the solution forward through the supply channels 32 to the chamber 24 and through into the outlet channel 36 into the waste reservoir 35, the aqueous amphiphilic molecule solution stream including slugs of air are passed over the wells 21. The process is repeated to achieve the desired number of passes.

Excess amphiphilic molecules are removed from the chamber 24 by flushing aqueous buffer solution from a reservoir 30 by action of an inlet pump 33. Multiple volumes of aqueous buffer solution passed through the chamber 24 into the outlet channel 36 for supply to the waste reservoir 35.

Preparation of the sensor device 14 is completed by flow of aqueous solution containing a membrane protein, for example alpha-hemolysin or a variant thereof, from a reservoir 30 by action of an inlet pump 33 into the chamber over the layer 26 allowing the membrane protein is inserted spontaneously into the layer 26 of amphiphilic molecules after a period of time.

In an alternative approach, the membrane proteins may be stored dried. In this case, the aqueous solution may be directed into a second reservoir 30 containing the membrane protein in dried form from an appropriate reservoir 30 by an inlet pump 33 via the supply channels 32 by altering the position of the selector valve 45 used to rehydrate the membrane proteins before using an inlet pump 33 to flow the resulting solution into the chamber 24 over the layer 26.

The insertion process into the layer 26 may be observed by monitoring of the resultant electrical signals across the electrodes 22 and 25 when a potential is applied insertion resulting in an increase in ionic conduction and an increases in the measured current.

When the insertion period is complete removed from the supply channels 32 and chamber 24 by flush of aqueous buffer solution from a reservoir 30 by action of an inlet pump 33. Multiple volumes of aqueous buffer solution passed through the chamber 24 into the outlet channel 36 for supply to the waste reservoir 35.

Analysis of the samples contained in the well plate 100 may start on completion of preparation of the sensor device 14. The rotary valve 110 is configured to allow fluid contact with the first inlet port 133. The selector valve 45 is positioned to stop flow from the fluid reservoirs 30 and the outlet pump 34 operated to draw the sample material from the sample well 102. The rotary valve 110 is repositioned to direct flow towards the supply channels 32 and fill the chamber 24 to cover the membrane layers 26 of the sensor system. On completion of the analysis the selector valve 45 is positioned to allow flow of aqueous buffer from the inlet pump 33 to flush the sample from the supply channels 32, the rotary valve 110 and the chamber 24 with multiple volumes of buffer through the outlet channel 36 into the waste reservoir 35 to prevent contamination of succeeding samples.

The selector valve 45 is positioned to stop flow from the fluid reservoirs 30 and valve 110 is repositioned to form fluid connection to the next sample well 102 in the well plate 100. This process repeated for all samples.

After all the samples have been analysed, either the cartridge 10 may be disposed of. Alternatively, as the well plate 100 is a separate element, it may be removed, disposed of and replaced by a new well plate 100 loaded with fresh samples. Such use of the well plate 100 as a disposable element allows re-use of the cartridge 10.

The sensor device 14 is formed in a chip that is mounted on a printed circuit board (PCB) 38 electrically connected to the PCB 38. Electrical contacts from the PCB 38 are arranged as an edge connector pad for making electrical connection to the sensor device 14. On insertion of the cartridge 10 into the module 2, the contacts 39 make electrical connection to the remainder of the electrical circuit in the module 2 that is described below. Three alternative designs for the sensor device 14 and PCB 38 are as follows.

Figure 5:
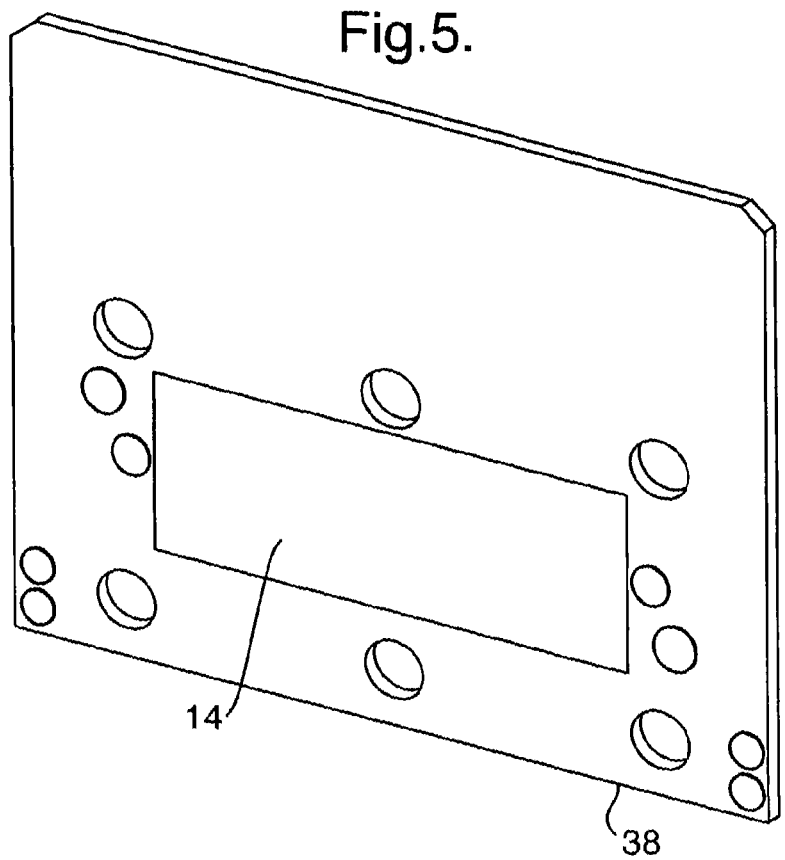
FIGS. 5 and 6 are top and bottom perspective views of the sensor device mounted on a PCB.
Figure 6:
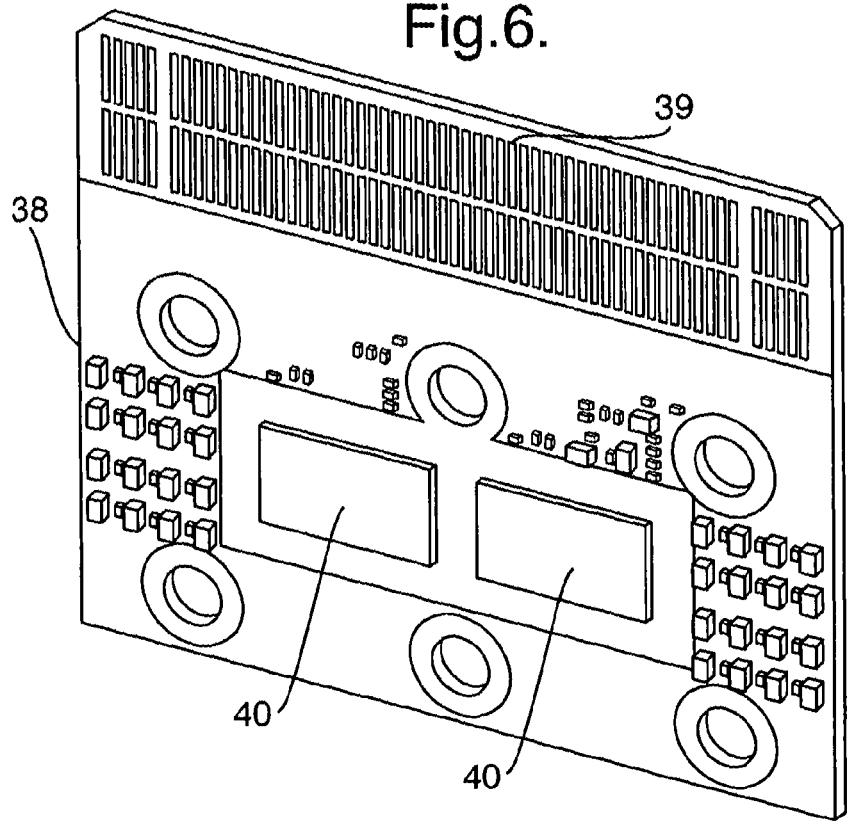

In the first possible design shown in FIGS. 5 and 6, the sensor device 14 is formed as disclosed in WO-2009/077734 as an array of electrodes embedded in wells fabricated on silicon with wells made in a suitable passivation layer on top of the silicon, with the electrical connections at the base of the silicon substrate using through wafer vias, solder-bump bonded to the PCB 38. The PCB provides has an equivalent number of connections to two (or in general any number of) application specific integrated circuits (ASICs) 40 bonded in similar fashion to the opposite side of the PCB 38. The ASICs 40 include some of the components of the electrical circuit of the module 2 described below. The ASICs 40 may include components of the processing circuit for processing the electrical signals from the sensor device 14, for example an amplifier, a sampling circuit and an analog-to-digital converter (ADC) to provide a digital output. The digital output is supplied from the contracts 39 to enable the digital output to leave the sensor device 14 using a suitable interface, for example low-voltage differential signalling (LVDS). Alternatively, the output signal may be provided in amplified analog form with ADC provided within the module. The ASICs 40 may also include some components of control circuits for example accepting power and control commands via the contacts in order to set and monitor functioning parameters, including for example current measurement sample rate (1 Hz to 100 kHz), integration capacitors, bit resolution, applied bias voltage.

The second possible design is to form the sensor device 14 as a simple electrode array chip fabricated on silicon, mounted on the PCB 38 and wire-bonded to the contacts 39. This connection can then interface into the electrical circuit, either as a series of discrete channels, or using an appropriate ASIC. Such an ASIC may be a conventional electronic readout chip, for example as supplied by FLIR Systems, (e.g. FLIR ISC 9717) as an arrayed electrode measurement device.

The third possible design is to fabricate the sensor device 14 and ASIC 40 as one device that is then mounted on the PCB 38.

Figure 7:
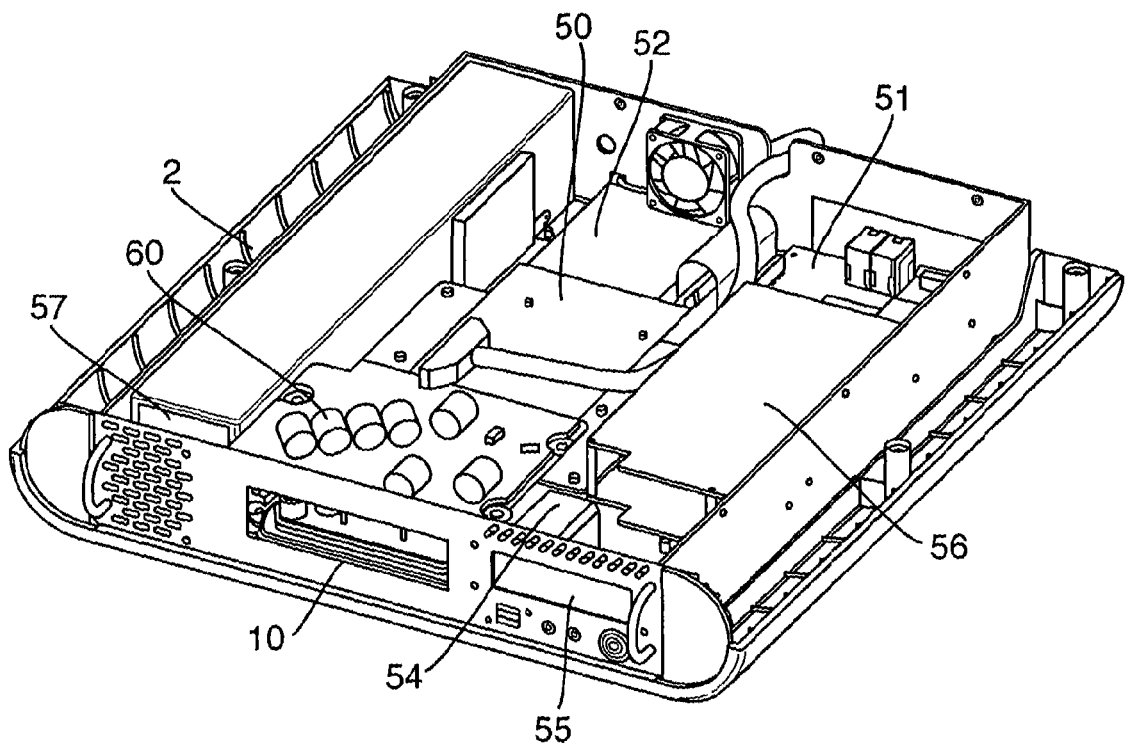
FIG. 7 is a perspective view of the module.

The configuration of the module 2 will now be described with reference to FIG. 7 which shows the module 2 with the housing 11 removed to show the physical layout. The module 2 includes an internal board 50 and an embedded computer 51 connected together by a PCI data acquisition module 52, which together provide an electrical circuit described below. The internal board 50 makes contact with the contacts 39 of the cartridge 10 on insertion into the module 2.

The embedded computer 51 may be a conventional computer, including a processing unit and a storage unit. The embedded computer 51 includes a network interface 53 that allows the module 2 to connect to the network 3, thereby turning the module 2 into a standalone network device yet also providing 'hooks' to enable many modules 2 to be run, managed and controlled as a cluster, as described below. For example, the embedded computer 51 may run a slimmed down operating system (e.g. LINUX) and applications to perform the various functions described below. Complete development kits for such embedded systems are commercially available.

The module 2 includes a loading mechanism 54 for automatically loading and ejecting the cartridge 10 to and from the module 2. The loading mechanism 54 may be for example a proprietary mechanism driven by a high precision stepper motors.

The module 2 also includes a microcontroller 58 and an FPGA 72 mounted on the internal board 50 that control various components of the module 2 as described below.

The module 2 also includes fluidics actuation unit 60 that is mounted on the internal board 50 and controls the fluidics system 31.

The module 2 also comprises a thermal control element 42 arranged to control the temperature of cartridge 10 and the sensor device 14 in particular. The thermal control element 42 may be for example a Peltier thermal controller, such as a 32 watt Single Stage Thermoelectric Module (for example as supplied by Ferrotec Corp, 33 Constitution Drive, Bedford N.H. 03110 USA—part number 9500/071/060B). The thermal control element 42 may be mounted, for example, underneath the cartridge 10 and so is not visible in FIG. 7. The thermal control element 42 may be considered as part of the analysis apparatus formed primarily by the cartridge 10 and could alternatively be mounted on the cartridge 10.

Lastly, the module 2 includes a display 55 for displaying basic operational status information, a power supply 56 for supplying power to the various components of the module 2, and a cooler assembly 57 for cooling the module 2.

The electrical circuit provided by the internal board 50 and the embedded computer 51 will now be described with reference to FIGS. 8 and 9. The electrical circuit has two main functions, namely a signal processing function and a control function, so that it acts as both a signal processing circuit and as a control unit for the module 2.

The signal processing function is distributed between the internal board 50 and embedded computer 51 and is provided as follows.

The sensor device 14 is connected to a switch arrangement 62 formed in an ASIC 40 on the PCB 38 of the cartridge 10 and controlled by the control interface to the ASIC 40. The switch arrangement 62 is arranged to selectively connect the well electrodes 22 of the sensor device 14 to a respective contact for supply to a detection channel 65 of the signal processing function, there being a greater number of wells 21 than detection channels. The switch arrangement 62 is arranged and operated as described in detail in U.S. Application No. 61/170,729 which is incorporated herein by reference.

Alternatively the switch arrangement 62 may be provided and controlled separately from the ASIC 40 as a standalone functional block between the sensor device 14 and the detection channels 65, the detection channels 65 being provided within a readout chip, for example as supplied by FLIR Systems, (e.g. FUR ISC 9717).

Figure 10:
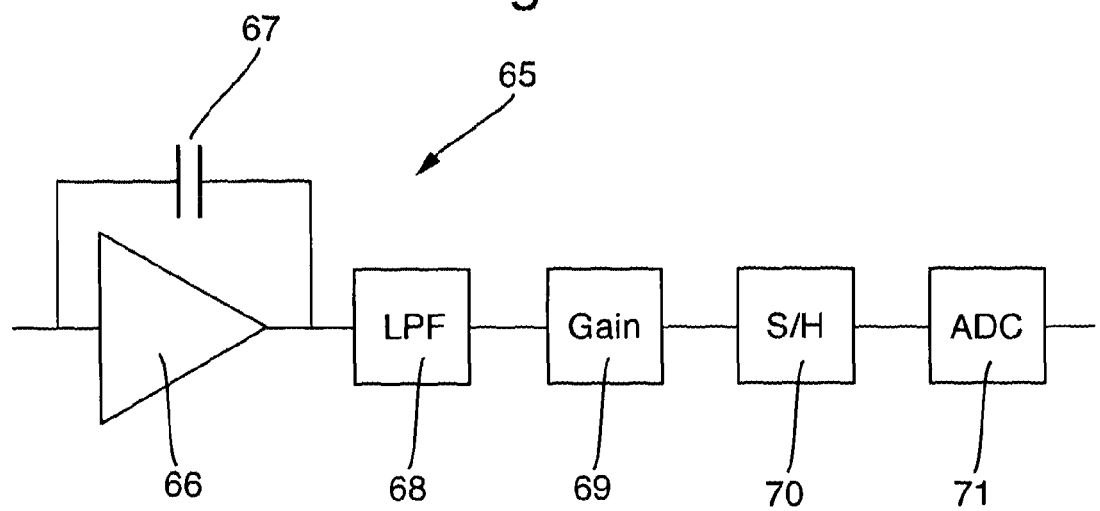
FIG. 10 is a diagram of a detection channel.

The ASIC 40 provides an array of detection channels 65 each arranged as shown in FIG. 10 to amplify the electrical signal from one of the well electrodes 26. The detection channel 65 is therefore designed to amplify very small currents with sufficient resolution to detect the characteristic changes caused by the interaction of interest. The detection channel 65 is also designed with a sufficiently high bandwidth to provide the time resolution needed to detect each such interaction. These constraints require sensitive and therefore expensive components.

The detection channel 65 includes a charge amplifier 66 that is arranged as an integrating amplifier by means of a capacitor 67 being connected between an inverting input of the charge amplifier 66 and the output of the charge amplifier 66. The charge amplifier 66 integrates the current supplied thereto from the well 21 to provide an output representative of the charge supplied in successive integration periods. As the integration periods are of fixed duration the output signal is representative of current, that duration being short enough to provide sufficient resolution for monitoring of events occurring in the well 21 connected thereto. The output of the charge amplifier 66 is supplied through a low pass filter 68 and a programmable gain stage 69 to a sample-hold stage 70 that is operated to sample the output signal from the charge amplifier 66 and produce a sampled current signal. The output current signal is supplied to an ADC 71 to convert it into a digital signal. The digital signals from each detection channel 65 are output from the ASIC 40.

The digital signals output from the ASIC 40 are supplied via the contacts 39 from the PCB 38 of the cartridge 2 to a field programmable gate array (FPGA) 72 provided on the internal board 50 of the module 2. The FPGA 72 includes a buffer arranged to buffer the digital signals from each detection channel 65 before supply via the PCI data acquisition module 52 to the embedded computer 51.

In an alternative arrangement, the digital output from the detection are provided from a readout chip located on the internal board 50 of the module 2 and supplied to the FPGA 72.

The embedded computer 51 is arranged as follows to process the digital current signals from each detection channel 65 as follows. A PCI data acquisition module 52 controls the transfer of the digital current signals from the FPGA 72 to the embedded computer 51 where it is stored as digital data.

Thus, the digital data stored in the embedded computer 51 is raw output data that is signal data representing the measured electrical signal from each detection channel 65, that is the current measured by each well electrode 22 in respect of a nanopore in the amphiphilic membranes 26 of the corresponding well. The current from each nanopore is a channel of the measured electrical signal. This raw output data is processed by a processing module 73 that includes a pipeline 74 in respect of each channel. The processing module 73 is implemented by software executed in the embedded computer 51.

The nature of the signal processing performed in each pipeline 74 of the processing module 73 is as follows. The pipeline 74 processes the raw output data representing the measured electrical signal to produce output data representing the results of the biochemical analysis in respect of the corresponding channel. As discussed above, interactions between the nanopore and the sample cause characteristic changes in the electrical current that are recognisable events. For example, an analyte passing through the nanopore may cause the electrical current to reduce by a characteristic amount. Thus, the pipeline 74 detects those events and generates output data that is event data representing those events. Examples of such processing are disclosed in WO2008/102120 which is incorporated herein by reference. The output data that is event data may in the simplest case represent only the fact that the event has occurred, but more typically includes other information about the event, for example the magnitude and period of the event.

Additionally, the pipeline may classify the event and the output data may represent the classification of the event. For example, the nanopore may have an interaction that differs as between different analytes in the sample causing a different modulation of the electrical signal. In this case, the pipeline 74 classifies the analyte on the basis of the modulated electrical signal. An example of this is that a nanopore may have an interaction with bases of a polynucleotide in which each base modulates the electrical signal differently. For example, a base passing through the nanopore may cause the electrical current to reduce by an amount that is characteristic of the base. In this case, the pipeline 74 classifies the event by identifying the base from the modulation of the electrical signal. In this manner, the biochemical analysis is sequencing of a polynucleotide in the sample, and the resultant output data is sequence data representing a sequence of the polynucleotide. This may be referred to as "base calling".

The pipeline 74 also produces output data that is quality data representative of the quality of the output data that represents the results of the biochemical analysis. This may represent a probability of the detection and/or classification of the events being incorrect.

The output data may be represented in any suitable format. In the case of sequencing of a polynucleotide, the output data that is sequence data and the quality data may be represented in the FASTQ format which is a conventional text-based format for a nucleotide sequence and its associated quality scores.

All of the output data is stored in the embedded computer 51 and some or all of the output data may also be transferred over the network 3 and stored on the storage device 6. Typically this includes at least the output data representing the classification of the event (e.g. sequence data) and the quality data, as this is a relatively small amount of data compared to the raw output data representing the measured electrical signal. Additionally and depending on the user's requirements, there may also be transferred and stored the output data that is event data, and/or the raw data representing the measured electrical signals across each nanopore.

The processing module 73 may also derive and store quality control metrics representing parameters of the biochemical analysis itself.

Aspects of the signal processing performed by the pipeline 74 may be performed on the internal board 50 before data is transferred to the embedded computer 51. This approach is of particular use for large numbers of channels and the FPGA 72 may be particularly suited to this type of task.

There will now be described the control function that is arranged to control the operation of the module 2. The control function is distributed between the internal board 50 and embedded computer 51 and is provided as follows.

The control function includes a controller 58, for example a Cortex M3 Microcontroller, provided on the internal board 50. The controller 58 controls the operation of all the components of the analysis apparatus 13. The controller 58 is arranged to send, via standard protocols and through low level device drivers, commands to the pumps 33 and 34 of the fluidics system 31 and other pre-requisites for reading data. Status information is stored based on error codes derived from drivers.

The controller 58 is itself controlled by a control module 80 that is implemented in the embedded computer 51 by software executed thereon. The control module 80 communicates with the controller 58 via an RS232 interface 81. The control module 80 controls the controller 58 as follows so that they operate together to constitute a control unit for the module 2.

The controller 58 controls the loading mechanism 54 to load and eject the cartridge 10. On loading the controller 58 detects that proper electrical contact is made between the contacts 39 and the internal board 50.

The controller 58 controls the fluidics actuation unit 60 to control the fluidics system 31 to prepare the sensor device 14.

During this preparation, the control module 80 may monitor the electrical signals output from the sensor device 14 to detect that preparation occurs correctly, for example using the analysis techniques disclosed in WO-2008/102120 which is incorporated herein by reference. Typically, the control module 80 will determine which of the wells 22 are set-up correctly at the start of a run. This may include sensing bi-layer quality, electrode quality, occupancy by a pore and even whether the nanopore is active following the sensing of a sample.

On the basis of this monitoring, the controller 58 also controls the switching controller 63 to cause the switch arrangement 62 connect detection channels 65 to the well electrodes 26 of wells 22 of the sensor device 14 that have acceptable performance, in the manner disclosed in detail in U.S. Application No. 61/170,729.

In the case of sequencing of polynucleotides, the control module 80 may also sense the presence and state of any modifications to nanopores that might be required in order to process and measure DNA, e.g. attachment of exonuclease enzymes, cyclodextrin adaptors.

The controller sets the following experimental parameters.

The controller 58 controls a bias voltage source 59 that supplies a bias voltage to the common electrode 25. In this way, the controller 58 controls the bias voltage across each nanopore. The controller 58 controls the thermal control element 42 to vary the temperature of the analysis apparatus 13. The controller 58 controls the operation of the ASIC 40 to vary the sampling characteristics, for example the sampling rate, the integration period and reset period of the capacitor 67, and the resolution of the resultant signal.

The controller 58 may execute the above control functions and other experimental parameters via the FPGA 72. In particular, control of the ASIC 40 is provided via the FPGA 72.

Once the sensor device 14 has been prepared correctly, then the controller 58 controls the analysis apparatus 13 to introduce the sample and to perform the biochemical analysis. The biochemical analysis is then performed with the result that electrical signals are output from the sensor device 13 and processed by the processing module 73 to produce output data representative of the analysis.

As described further below, the control module 80 has local performance targets that are derived on the basis of input as discussed below. The local performance targets represent the desired performance for the operation of the module 2. The performance targets can relate to any combination of: the time within which output data is produced; the quantity of output data that is produced; or the quality of output data that is produced, depending on the requirements for the biochemical analysis.

During operation, the control module 80 determines, from the output data, measures of performance of the biochemical analysis, these being of the same nature as the local performance targets, i.e. the time within which output data is produced; the quantity of output data that is produced; or the quality of output data that is produced. On the basis of the measures of performance, the control module 80 controls the controller 58 to control the analysis apparatus 13 to meet the performance targets. This is done by starting and stopping operation of the analysis apparatus and/or varying the operational parameters. To meet the local performance targets, the controller 58 controls the following operational parameters that affect performance, in terms of speed of data collection and quality:

1) the thermal control element 42 to vary the temperature of the analysis apparatus 13. This affects the biochemical analysis occurring in the sensor device 14, for example by changing the rate of movement of molecules through the nanopore and/or the rate of processing by enzymes, for example in the case of sequencing the enzyme that feeds bases sequentially through the nanopore. Typically, the increase of the temperature increases the data collection rate but decreases the quality, and vice versa.

2) the bias voltage source 59 to vary the bias voltage across each nanopore. This is an electrical parameter of the biochemical analysis that affects the performance and can be varied to alter speed and quality, or used to 'fine-tune' a nanopore to focus high quality measurement for a particular analyte.

3) the operation of the ASIC 40 to vary the sampling characteristics, for example the sampling rate, the integration period and reset period of the capacitor 67, and the resolution of the resultant signal. These affect the quantity and quality of the output data. Typically, increase of the sampling rate reduces the chance of missing real events, but increases noise causing poorer quality of measurement of each observed event, and vice versa.

To meet the local performance targets, the controller 58 also controls the operation of the analysis apparatus 13, for example:

4) the bias voltage source 59 to vary the bias voltage across each nanopore. This is an electrical parameter of the biochemical analysis than affects the performance;

5) to control the switch arrangement 62 to change the nanopores whose electrical signals are supplied to the detection channels 65;

6) to add more fluids; to add more nanopores to a functioning array of amphiphilic membranes 26 with none or some nanopores present;

7) to add more sample if the sensor device 14 as a whole is making insufficient measurements;

8) to add a different sample if the measurement requirements for one sample have been met;

9) to apply a reverse bias potential to 'unblock' a nanopore in the case of zero current flow in an individual nanopore;

10) to reset the analysis apparatus 13, either if a global failure setting on chip has been reached, or if required before a new sample to be measured is introduced, or if a different type of nanopore is needed to measure the sample, by applying a bias potential sufficient to rupture all the amphiphilic membranes 26 and then preparing the analysis apparatus 13 again.

In the case of sequencing of polynucleotides, the analysis apparatus 13 may contain control DNA spiked into real samples. This also allows for quality monitoring of the status of individual nanopores. Data derived from the control sample spike can also be used to adjust and refine the algorithms used to process the data originating from real DNA samples proceeding in parallel.

The control module 80 may also control the signal processing function, for example to control the pipelines 74 to perform varying degrees of data processing.

The control module 80 performs the determination of measures of performance and control of the operation repeatedly during the biochemical apparatus, typically continuously. In this manner, the operation of a single module 2 can be optimised in real time with the result that the module 2 is more efficiently utilised. When the control module 80 determines from the measures of performance that the biochemical analysis has been completed, the control module 80 controls the controller 58 to stop the biochemical analysis and controls the loading mechanism 54 to eject the cartridge 2. The module 2 is then ready for insertion of a new cartridge 2, which may be performed by an automated procedure as part of the overall workflow pipeline for an experiment or series of experiments being performed by the instrument to meet the global requirements of the user.

In the manner described above, each module 2 is a standalone device that can perform a biochemical analysis independently of the other modules 2. There will now be discussed how a cluster of modules 2 are operated as a common instrument 1 to perform a common biochemical analysis. This is achieved by a cluster of modules 2 being connected together over the network 3 via the network interface 53. In overview, the module 2 connects to the network 3 as a self-aware network device following the widely used "appliance" model. The module 2 can thus run data and communication services. Configurations and protocols are stored and run as part of the control module 80. Each module 2 can operate as both a client to services and data, and as a server for data and services, to any other module 2. Thus arbitrary number of modules 2 can be clustered together into a larger logical instrument 1.

The modules 2 may also communicate to share other information, such as dynamically determined calibration criteria, enabling consistent data quality from each module 2, or filtering rules for output data, shared output locations and conflict free concurrent output of data from the same named substrate to a shared repository.

Each module 2 includes a web services module 82 that provides a graphical user interface (GUI) and a federation/control application programming interface (API).

The GUI is presented over the network 3 to the external computer 7 and displayed thereon. For example the GUI may be presented in HTTP on the standard HTTP port or in any other format allowing it to be viewed by a conventional browser. The user may view the displayed GUI and connect to this web service using standard protocols (e.g. HTTP) to use the GUI to provide user-input to the modules 2. The GUI may be a series of web pages that allow control of the modules 2, input of parameters, shows statuses, graphs data etc. The user is able to see the status of the module 2 they have selected and send it commands via this interface. This same service runs on all modules 2 and can be connected to in the same fashion. The GUI may be replaced by any other suitable interface, for example a command line.

The API allows the modules to interact with each other.

The GUI allows the user to address the modules 2 to select an arbitrary number of modules 2 to operate as a cluster to perform the common biochemical analysis. Each module presents the GUI, so any module 2 can be accessed by a user and used to select multiple modules 2. This causes the API to send a single command to all of the modules in the cluster 2 informing them that they are addressed. The modules 2 selected for the cluster are given a temporary and arbitrary label, referred to as a "namespace", identifying them mnemonically to both the control module 80 and user as a cluster doing the common biochemical analysis.

Furthermore, the GUI allows the user to provide input representing global performance targets in respect of the instrument 1. Alternatively, input representing the global performance targets may be derived by the instrument 1, for example being retrieved from a stored table of global performance targets in respect of different types of biochemical analysis.

The global performance targets are of the same nature as the local performance targets, that is any combination of: the time within which output data is produced; the quantity of output data that is produced; or the quality of output data that is produced, depending on the user's requirements for the biochemical analysis. The global performance targets may be fully defined, or some may be left undefined, for example a requirement to produce a certain amount of data of a certain quality is achieved by setting the quantity and quality targets but leaving the time target unset. For example, the modules global performance targets might be to acquire enough data to cover (or over-sample) the sample in question 20 times over, in a given period, say 6 hours, and with a minimum required level of data quality, say a minimum average error rate of less than one in one thousand across all bases measured.

Subsequently, cartridges 10 are prepared with aliquots of the sample to be analysed and loaded into the modules 2 of the cluster. This step may be performed by the user. Alternatively, this step may be automated to some extent, for example by the module 2 having a sensor that provides for automated registration of the cartridges 10. Then, a command is issued to the modules 2 of the cluster instructing them to start the analysis.

In advanced systems, the preparation of the cartridges 10 with sample to be analysed and/or the loading of cartridges 10 into modules 2 may be automated.

In another alternative, the cartridge 10 contains a mechanism to manage and process multiple samples in series, or time multiplexing, as for example with the construction shown in FIG. 11, using well plate 100 to store multiple samples to be processed by the sensor chip 14 in series. In this case each module 2 controls the cartridge 10 loaded therein to process samples from a selected wells 102. The software on the module 2 is set by the user, for example by receiving user input, to be aware of which samples are in which wells 102. This adds a layer of information to the sample management. All other operations of the cluster remain the same, save that the co-ordination now also takes into account which samples are being processed from a given well 102 on the plate 100 rather than assuming there is a mapping of one sample to each cartridge 2. Thus the co-ordination occurs at the level of samples per plate 100 rather than samples per cartridge 2. When a new cartridge 2 is inserted, the control module 80 references the sample-well table loaded by the user. This may also be accessed from a central database using an internal barcode provided on the cartridge 2 as a lookup key (the plate and sample information having been associated with this cartridge by a user at the time the well plate 100 was attached to the cartridge 2).

The modules 2 of the cluster are now 'aware' that they are cooperating and their control modules 80 communicate and interact as follows so that they together provide a control system for the instrument 1 as a whole.

Figure 23:
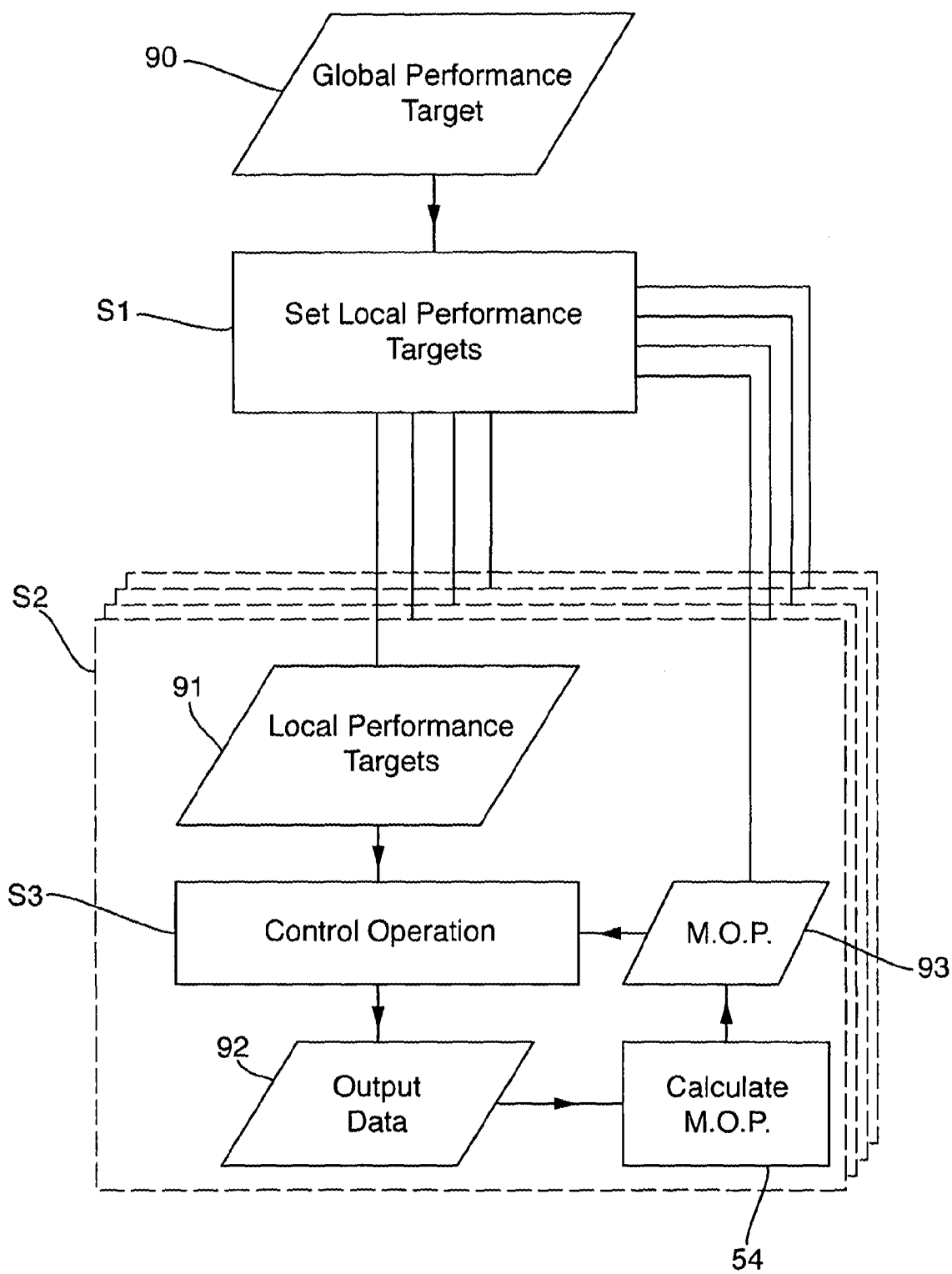
FIG. 23 is a flow chart of the control process of the instrument.

The control process is shown in FIG. 23.

In step S1 there are determined, on the basis of the global performance targets 90, local performance targets 91 for each module 2 in the instrument 1 that together meet the global performance targets 90. Step S1 is a global determination performed for all the modules 2 in the cluster. Initially, step S1 is performed on the basis of the global performance targets 90 alone, although as discussed below, subsequently S1 is also performed on the basis of measures of performance 93 of each module 2 in the cluster derived from the output data 92 of each module 2.

Step S2 is performed a local control process in respect of each module 2 in the cluster, performed on the basis of the local performance targets 91 for that module 2. In FIG. 23, four such local control processes are shown by way of illustration, but in general there are the same number of local control processes as modules 2. The local performance targets 91 effectively indicate the operation that is required from each respective module 2, and in step S2, each module 2 is operated in accordance with the local performance targets 91 to provide that required operation, so that the modules 2 together perform the common biochemical analysis.

Step S2 itself comprises the following steps.

In step S3, on the basis of the local performance targets 91, the operation of the analysis apparatus 13 is controlled in the manner described above, that is by starting and stopping operation of the analysis apparatus and/or varying the operational parameters.

Initially, step S3 is performed on the basis of the global performance targets 90 alone. However, once operation has started, output data 92 is derived. As part of the local control process of step S2 in respect of each module 2, in step S3 there are derived measures of performance 93 from the output data 94, as described above. Then in the local control process of step S2 in respect of each module 2, step S3 is performed on the basis of the measures of performance 93, as well as the local performance target 91. In this manner, the control of the operation of each module 2 is varied on the basis of the measures of performance 91 that are actually being achieved by the module 2. The control performed in step S3 is updated in this manner by feedback of the measures of performance 93 derived from the output data 92 repeatedly, and typically continuously during the performance of the biochemical analysis.

In addition, at least once during the performance of the biochemical analysis, the measures of performance 93 from all of the modules 2 in the cluster are fed back to step S1. Then, in step S1, on the basis of measures of performance 93 from all of the modules 2 and the global performance targets 90, the local performance targets 91 are varied, if necessary to meet the global performance targets. The respective modules 2 are then operated in step S3 in accordance with the updated local performance targets 91. Updating of the local performance targets 91 effectively indicates that the operation required from each respective module 2 has changed. Operation of the modules 2 under the control of the control modules 80 in accordance with an updated local performance target 91 varies the required operation of the modules 2 to meet the global performance targets 90.

Such update of step S1 to vary the local performance targets, if necessary, is performed at least once, but is preferably performed repeatedly, preferably periodically, and preferably with an interval that is much greater than the period of the biochemical analysis, typically by at least an order magnitude, and much greater than the period at which the control of the operation of the modules in step S3 is updated, typically by at least an order magnitude. Increasing the frequency of the update, improves the management of the modules 2 but this is at the expense of occupying resources of the embedded computer 51 and the network 3 and the improvement reduces as the interval approaches a characteristic interval for an event of the biochemical analysis. Typically the interval might be of the order of 1 to 5 minutes, but the management of the modules 2 is still effective at longer intervals, say of the order of hours. But even performing the update once during the biochemical advantage provides an advantage over a monolithic apparatus.

In step S1, when attempting to set or update the local performance targets 91, it is possible that required operation is not achievable, that is because the local performance targets 91 of the modules 2 required to meet the global performance targets 90 are not achievable. To deal with this, the control modules 80 are arranged to determine if this is the case and to take remedial action. A variety of remedial action is possible.

One type of remedial action is to increase the number of modules 2 in the cluster used to performing the common biochemical analysis. This allows the global performance target 90 to be met. To achieve this, the control units 80 may produce output notifying a user. In response, the user may use the GUI to address one or more additional modules 2 to form part of the cluster and set up those modules 2 in the same manner as the original modules, including introduction of a sample into a cartridge 10 and loading of the cartridge into each of the one or more additional modules 2. Alternatively any of these steps may be automated.

Another type of remedial action is to control the modules 2 of the cluster to stop the biochemical analysis altogether. This frees up the modules 2 for another biochemical analysis given that the global performance target cannot be met.

The decision-making in steps S1 and S3 may be an execution of any suitable computational method. The simplest of approach is to use a look up table, stored in the embedded computer 51, of contingencies to be carried out in given scenarios. Fore example, one such scenario might be an inability to meet a certain set of performance criteria because of one under performing node, for which the action may be for the other nodes to increase their rate of data acquisition. Straightforward programmatic logic could be used to analyse the data and derive a decision, coded in software. Other more complex methods may include the fuzzy recognition of certain patterns in the data and the generation of a response, e.g. via a trained neural network.

There will now be discussed where the various steps of the control process shown in FIG. 23 are implemented.

Step S2 is a local control process in respect of each module 2 that is performed on the basis of the local performance targets 91 for that module 2 and involves calculation of the measures of performance 93 from the output data 92. Therefore the control module 80 of each module 2 advantageously performs the local control process of step S2 in respect of its own module. In this manner, the control of operation in step S3 and the determination of the measures of performance 93 may be performed locally in the module 2 without the need to transmit any data across the network. This assists the scalability of the control process with the number of modules 2. Each module 2 performs the local control process of step S2 independently, and thus any number of modules 2 may be included in the cluster without an increase on the burden on the data transfer over the network 3 being needed to implement the local control process of step S2. This also effectively shares the processing load of step S2 between the modules 2 as each control module 80 performs its own processing.

In principle, step S3 or step S4 could be implemented in respect of one or more modules 2 externally, that is within a different module 2 or a further computer connected to the network 3. To perform step S4 externally, it would be necessary to transmit derived across the network 3 the output data from which the measures of performance 93 are. Similarly, to perform step S3 externally, it would be necessary to transmit derived across the network 3 the measures of performance 94 and control signals for the module 2. This would increase the burden on the network, especially as the control is varied in step S3 frequently. For any practical implementation of the network 3 and the external processing, this would create bottlenecks, in terms of either or both of the data transfer and the processing. Such bottlenecks would reduce scalability by effectively limiting the number of modules 2 that could be incorporated in a cluster.

There is an increased degree of flexibility in where step S1 is implemented. Step S1 does require the measures of performance 94 of all the modules 2 to be taken into account and as a result there must be some transfer of data over the network 2 so that step S1 may be performed on the basis of the measures of performance 94. However, the amount of data needed to be transmitted is relatively small, being the measures of performance 94 and messages to implement the negotiation between the control modules 80. This requires a significantly smaller amount of data than the output data itself. For example, the measures of performance simply represent the value of each measure, of which there are only a handful, whereas amount of the output data that is sequence data will be large, the amount of output data that is event data is typically an order of magnitude greater than the sequence data, and the amount of output data that represents the measured signal is typically an order of magnitude greater than the event data. Furthermore, it is noted that as step S1 is updated at a period much greater than the period at which the control of the operation of the modules in step S3 is updated, the frequency at which data that needs to be transferred across the network 3 is lower, which further causes the burden on the network 3 to be much lower than if step S2 was implemented externally of the modules 2.

In a first implementation, the processing of step S1 is shared between the control modules 80 of the modules 2 in the cluster. In this case, the control modules 2 co-operate with each other to perform step S1 to determine local performance targets 91 for each module 2 in the instrument 1 that together meet the global performance targets 90. This may be achieved by an iterative process. Each control module 80 derives its own proposed local performance targets and then communicates that to the other modules 2 in the cluster. On receipt of the proposed local performance targets from all the other modules 80, each control module 80 determines whether the global performance targets are met and if necessary revises its own proposed local performance targets. This process is repeated until the local performance targets have been agreed.

When step S1 is performed initially, this occurs on the basis of the global performance targets 90 alone because as yet no output data has been generated. When step S1 is performed subsequently to update, if necessary, the local performance targets of each module 2, step S1 is performed on the basis of the measures of the performance 94 derived by the control modules 80 of each module 2 in respect of that module 2. For this purpose, the control modules 80 communicate the measures of performance 94 to each other over the network 3. In this manner, the control modules 80 actively report the measures of performance 94 to one another in order to complete the biochemical analysis most efficiently. Each module 2 may reach its own decision. Decisions may then be coded into a lookup table present on each module 2. Each module 2 then transmits, via web service, its decision to the other modules 2 so that each module 2 now stores a table of the other modules 2 proposed responses. Having collated this table a simple majority vote can be applied to choose the proposed course of action if more than one is signalled.

Thus, the control module 80 of each module 2 is capable of performing the computations and decision-making required without user input, but they are also collectively able to do the same in concert. They can also share individual internal decisions, and collectively make meta-decisions, at a level above that, about the overall outcome. In this manner the federation/control API federates the decisions making across the modules 2 in the cluster in order to optimise a laboratory workflow.

In this manner, the modules 2 in the cluster making up the instrument 1 produce output data of plural channels from a common biochemical analysis. Optionally, the modules may include a federation layer (not shown) to allow the consistent filtering, normalisation and aggregation of that output data. In the case of sequencing of polynucleotides, the modules 2 can be controlled to perform sequencing analysis together in concert on single samples at high-throughput; such that each module 2 is equivalent to a sub-channel or 'lane' on a typical flow cell-based optical measurement DNA sequencing instrument.

This first implementation assists the scalability of the control process with the number of modules 2. Each module 2 contributes equally to step S1, so the processing load is shared equally and the processing load on a single module 2 is increased minimally by an increase in the number of modules 2 in the cluster. Increasing the number of modules 2 in the cluster merely increases the amount of data transmitted over the network in proportion to the number of modules 2. This will in principle eventually limit the size of the cluster for any given practical network 3, but the amount of data is relatively low, so in practice large numbers of modules may be accommodated.

As each module 2 participates in the decision-making process in this first implementation, this shares the processing load and has the advantage that the instrument 1 can be formed from any combination of modules 2 because they all have the capability for decision-making. However, the decision-making can be shared in different manners.

In a second implementation, the processing of step S1 is performed by the control unit 80 of just one of the modules 2 acting as a master, or by the control units 80 of a subset of the modules 2, to make decisions on the local performance targets 91 of every module 2 in the cluster, based on the measures of performance 94 communicated from the other modules 2. This still requires data representing the measures of performance to be transmitted over the network 3, and increases the processing burden on the module 2 acting as the master. Ideally any module 2 has the capability of acting as a master, so that a master is arbitrarily selected from whichever are modules 2 addressed as a cluster. Alternatively, only special modules 2 may act as a master, but this has the disadvantage of requiring to the user to select one of the modules 2 in every cluster that is addressed.

In a third implementation, the processing of step S1 is performed by a further computer that is connected to the network 3, such as the external computer 7 or a dummy module 2 that does not have an operative analysis apparatus 13, to act as a federation control unit to make decisions on the local performance targets. In this case, the further computer becomes part of the overall control system and the measures of performance are communicated from the modules 2 to the further computer to form the basis of the decision-making. However, the requirement for a suitably programmed further computer is itself a disadvantage in the sense that the modules 2 in isolation are not sufficient to implement the control. On the other hand, this implementation does reduce the processing requirement on the modules 2 themselves.

Another alternative is for additional nested levels of feedback are introduced into the control process shown in FIG. 23. In FIG. 23, there is feedback of the measures of performance 94 at two levels, firstly at the level of the local control process of step S2 for a single module and secondly at the level of the cluster as a whole. Additional levels may be introduced by dividing the modules 2 of the cluster into logical groups of modules 2 that are each subsets of the total number of modules 2 in the cluster. Performance targets and measures of performance for each logical group are derived in the same manner as the local performance targets and measures of performance for an individual module 2 as described above. Step S1 of the control process shown in FIG. 23 is modified to include an additional level of feedback. That is, at the highest level, the group performance targets are determined on the basis of the global performance targets and the measures of performance of each group. At the next level, in a separate group control process in respect of each group, the local performance targets of each module 2 in the group determined on the basis of the group performance targets and the measures of performance of each module 2 in the group. Similarly, measures of performance of the group as a whole are determined from the measures of performance of each module 2 in the group. In general, any number of nested levels of feedback may be employed, for example by dividing groups into sub-groups and so on.

In this case, the additional levels of feedback may be implemented using any of the implementations for the step S1 as described above.

This alternative does increase the complexity of the control process, but has the advantage of allowing the control process to be adapted to the nature of the common biochemical analysis and/or to different network structures. The different levels of the control process may be implemented in different elements of the instrument 1 and may be updated at different periods, with consequential reductions on the burden on the network 3. This. For example, the groups may be groups of modules 2 performing the same part of the common biochemical analysis that is advantageously controlled with reference to a group performance target for the entire group. Alternatively, the groups may be groups of modules 2 that are connected to respective local networks that are interconnected, e.g. over the internet, in which case the flow of data between the local networks is reduced without impacting the control of any individual group attached to a local network.

There will now be discussed the manner in which the modules 2 connect to the network 3 and communicate on a peer-to-peer basis. Generally speaking, the interchange of state data between modules 2 to facilitate primarily automated decision-making for performance management is performed on the basis of "eventual consistency" as a low update frequency is acceptable.

The modules 2 may identify each other using a service discovery protocol, for example Universal Plug and Play (UPnP) or Zeroconf (or Bonjour).

Metadata such as proposed local performance targets and the measures of performance may be propagated using a variety of types of distributed database techniques such as CouchDB (HTTP, JSON), Tokyo Cabinet, or MemcacheDB.

Alternatively, discovery and metadata propagation may be achieved using messaging techniques such as network broadcast, network multicast, The Spread Toolkit, ActiveMQ, RabbitMQ, or message queues in general.

One possible implementation is to use one perl script which runs in publisher, subscriber or pub+sub mode to implement network broadcast of beacon packets using User Datagram Protocol (UDP), each beacon packet containing encoded JSON (plain text javascript object notation) data. Each module 2 acts as a node that broadcasts its own details and listens for others. Received beacon packets are decoded and incorporated in an internal in-memory data structure, such as a hash keyed on the module name. This has the advantage of simplicity, the beacon packets containing at the very minimum, peer name (hostname by default), peer time and system performance & state data. Then modules 2 retransmit their entire data structure including data received from other modules 2. As UDP packets are unreliable and delivery of beacon packets is not guaranteed this retransmission improves the likelihood of a module 2 receiving data from other modules 2. As beacon packets may include data for all modules 2 in the cluster, modules 2 never incorporate external data purporting to be from themselves.

UDP packets are most efficient up to the maximum transmission unit (MTU) of the subnet. By default this is around ~1500 bytes. Compression of the payload (e.g. using common gzip/LZW) may be useful to keep transmission size under the MTU. With a fixed beacon frequency, as the number of modules 2 in a cluster increases there is a much greater risk of network packet collisions and retransmissions causing congestion and loss of bandwidth. This can be dealt with by using a dynamic beacon frequency inversely proportional to the number of active modules 2.

The advantages of the instrument 1 are that efficiency gains are achieved as compared to a monolithic instrument due to the modularisation of the analysis apparatuses 13 themselves and due to the operation of the individual modules 2 being intelligently parallelised. The user has a parallelized group of modules 2 at their disposal and can group a cluster of any number of such modules into a larger instrument 1 to meet the requirements of the common biochemical analysis that it is desired to perform. This scalability allows the performance of biochemical analysis of a range of complexity without being constrained by the capability of a single instrument. Similarly the control of the operation of the modules 2 optimises their performance to meet the global targets. Both these factors produce efficiency gains, because better use is made of the individual modules 2, effectively freeing up other modules 2 to perform other tasks.

For example a small number of modules 2 or even a single module 2 may be used for lower throughput applications and large clusters may be used for massively parallel applications such as large sequencing projects, e.g. sequencing of a human genome. This allows management of workflows that provides efficiency gains in the utilisation of equipment. In the specific case of sequencing, the resulting workflows overcome problems with current monolithic DNA sequencing instrumentation and meet the needs of users performing large genome sequencing projects where high throughput is required, whilst also fitting with the needs of intermediate labs doing smaller but highly replicated or heterogeneous designs, or just smaller experiments.

The instrument 1 may be applied with a different number of modules 2 to perform a range of types of analysis, for example:

Human Genome Re-sequencing/assembly.

Low coverage methylation or cancer re-arrangement

A highly replicated short read experiment, such as gene expression.

A single molecule analysis using a small sample or mixed cell population.

There will now be described some specific examples of situations where efficiencies are obtained:

1) A user sets up a cluster of ten modules 2 to measure DNA from a single sample. The user sets up the experiment such that 10 aliquots of sample are added to each module 2 to provide the necessary sample material, and after selecting his preferred settings (e.g. time to completion, data quality etc) begins the experiment. One module 2 has a faulty chip and is reporting very little data. The user has asked for experiment completion in a certain time, therefore the other nine modules 2 in the cluster increase their sequencing rate, via automatic manipulation of temperature to speed up each nanopore's processing speed, in order to meet that target Without this dynamic readjustment, the experiment would have completed in the set timeframe, but would have generated less data than expected by the user, potentially compromising his results and overall experimental outcome.

2) In another case, the user creates a cluster of 8 modules 2 to measure a single sample, again aliquoted across the 8 modules 2. Four of the eight modules 2 are reporting very low data quality and the other 4 cannot compensate due to the pre-specified performance parameters required by the user (for example output and quality of measurement). Therefore the faulty modules 2 terminate their runs and email the operator with a report of what has been done and why, thus allowing the operator either to enable a refresh of the nanopores in the same chips within the faulty modules 2 with alternate aliquots of sample with minimal loss of time or cost to the user, or to load another set of four chips immediately, which will minimise any loss of time. In this example the faults could be detected early in the runs and additional chips could be loaded before the time budget for the completion of the sample had lapsed thus salvaging the project. By comparison, if a user was performing the same experiment in Illumina's Genome Analyser, and four of its eight 'lanes' had faults causing low data quality production, the user can only either terminate the entire experiment early on, losing all data generated across all lanes up to that point in time, or allow the run to finish and only end up with approximately half the expected amount of high quality data, but at the same cost and taking the same amount of time as a fully functional experiment.

3) As a continuation of the scenario above, another useful situation could occur. The user's lab in question only has eight modules 2 installed, and the four failed ones have been ejected. But another urgent project is in a 'queue' to be run on the system. The operator can then make a decision to allow more time for the completion of the original project on the remaining modules 2 and to use the 4 freed-up modules 2 to process the waiting project as expediently as possible. Thus resources can be globally fitted to a laboratory's priorities.

4) A user wishes to perform an experiment on a sample, or an array of samples, looking for a particular result in them. The user may therefore specify that experimental processing of the sample or samples continue until a particular datum (e.g. an exact DNA sequence motif) has been observed once, or a specific number of times. In particular, a datum could be used as a marker or proxy for the likely overall success of the experiment once the full data set has been analysed. For example, coverage of a certain level of a particular region of the genome is known, from previous sequencing runs using the same library of DNA fragments, to ensure a total coverage (degree of over-sampling) across the entire sample sufficient for the study that the user requires. On a cluster of modules 2 such a search can be shared across the modules 2 and when enough data of the required type has been observed this can be used to set a stopping condition for some or all of the participating modules 2. This optimisation of time and cost to reach an experimental outcome cannot be performed on current DNA sequencing instrumentation.

5) A user has set a requirement for a cluster of modules 2 to analyse a DNA sample at a pre-specified high quality. During the experiment, the modules 2 collect data in higher quantity than expected by the user, but not with high enough quality. In order to reach the required quality goal faster, the modules 2 collectively adjust their analysis conditions to improve data quality, even if this is at the expensive of throughput (given data quantity has been over achieved already). For example, by reducing the operating temperature, DNA bases move through each nanopore more slowly, on average, thus enabling more analysis time per base, which improves the quality of base measurement, albeit at a slower yield of data per nanopore. Alternatively, or in parallel, the rate at which current flowing through each nanopore is measured can be altered, either sampling faster or slower, which may improve particular aspects of data quality, depending on signal to noise profile and the speed of bases through the nanopore.

6) One module 2 in a cluster during an experiment experiences a catastrophic hardware failure, and is safely shutdown with causing a loss of experimental data (n.b. all data generated by the module 2 up to the time of fault is useable and has already been passed into a dedicated storage area). All remaining modules 2 respond by increasing their expected experiment timeframe in order to meet the user's preset needs of a required data output without user intervention. The system also sends an automated message to the manufacturer to order a replacement product. Minimal disruption to the user's experiment and workflow has occurred.

In the case where a cartridge 2 is capable of processing multiple samples, as for example with the construction of FIG. 11, examples of global performance targets that can be met are as follows:

1) A sample is being processed on a plate 100 on a node in a co-operating cluster. The user has specified that a certain amount of data is required. The sample exists on another plate 100 and is also being processed by another cluster node. The modules 2 co-ordinate as previously described.

2) The scenario as shown in 1 is followed but in this case the second sample on the second plate 100 is of poor quality. The module 2 responds to the performance target by scanning the internally stored plate-sample table to see if another instance of the sample exists on its plate 100, if so it then resets its valve to use this sample rather then the depleted one and the co-ordination continues.

3) In another example, ten modules 2 are processing identical plates 100 of sample and working through them. A user changes the priority of one of his/her samples that has not yet been processed. Some of the modules 2 of the cluster now reset their valves to move onto that sample in order to deliver its data on time. The remaining modules 2 of the cluster continue on the original samples and speed up their rate of processing by altering temperature.

4) In another example, a cluster of modules 2 are processing identical plates. Before they begin they set their valves 110 to move through the wells 102 where they take a sip of the sample and perform a short run. From this they then together, pre-calculate the likely data quality and quantity arising from each sample (or well 102). They then, together, compute the optimal sequence in which to process the samples in order to deliver data of the required quality and quantity to their respective users in line with preset priorities. If wells 102 were found to be empty, or the samples are of too poor quality to meet the targets, the cluster notifies the users that fresh plates need to be made with the dud samples re-prepared.

A key enabler is the ability of the modules 2, individually and in concert, to decide a sufficient, and sometimes preset, stopping condition. This ensures that neither too little nor too much data of the required quality is generated. In this way full occupancy of the systems can be achieved, and no 'slack' data is produced in the case of excess. Nor does an extra whole run have to be performed post-hoc in order to adjust for any deficiencies in output or quality. This general scheme allows samples and data to be efficiently pipelined through the entire sequencing workflow optimising throughput, quality and costs. For any high-end lab this can achieve several fold improvement in efficiency over systems that operate fixed run times with fixed data yields, especially if those data yields are not always predictable, as is normally the case.

It is noted that all of the above operations are enabled and performed by the specific control implementation shared within each module 2. It is also noted that modules 2 can be run individually and some, but not all of the above scenarios can be enacted on one module 2. Internal optimisations can be enacted, but optimisations across several modules 2 cannot.

The operation of the instrument in example (1) will now be described in more detail.

In this case the instrument 1 being used for DNA sequencing. This means detecting at least four possible analytes corresponding to the bases G, C, A and T. Ten modules 2 are being used and the they have been given the same sample to process. The user requires that 12 Gigabases ($10^9$) of data are required in 1 day where 100% of the recorded bases have a quality score of Q20 or higher (i.e. a base has less than a 1 in 100 chance of being incorrect). The amount of data and the quality of the data have been chosen to ensure that when the DNA sample is analysed it is almost certain that the user will be able to find the genetic elements (e.g. mutations they are looking for). These criteria may have been derived from prior empirical experience or from some simulations.

The user has at least ten modules 2 in suitable locations and knows the network addresses of the embedded computer 51 within each module 2. The user prepares their DNA sample in a manner appropriate for the given experiment. If this were sequencing a Human genome they might randomly shear a sample of the DNA using suitable off-the-shelf equipment.

The user has decided, based on the likely throughput (data per unit time) to use ten modules 2 for this sample. The sample is introduced into ten cartridges 10 which are loaded into the modules 2. The modules 2 might automatically read a barcode or RFID on each cartridge 10 uniquely identifying the cartridge 10 and store the ID of the cartridge 10.

The modules 2 identify other modules 2 in the cluster and send a handshake and receive basic information about the other modules 2. This information is then displayed in the GUI. In this example the user can see the twenty modules 2 on this network, but is only interested in the ten with cartridges 10 loaded containing his sample. These are identified via the GUI by name, address, status, location etc all of which are collated from the underlying web-services. Any module 2 can be used to manage any other module 2 in this fashion and no other computer is required. Thus any arbitrary number of modules 2 can be connected, managed and run in a linearly scalable fashion without the bottleneck of working through a gateway system.

The user now addresses the ten modules 2 of interest via the GUI. A GUI element allows a name to be assigned (e.g. 'Human'). The same GUI allows commands to be addressed only this collection and for any data returned from these module 2 to be treated as an aggregate and independently from any other cluster of modules 2. The user may also enter other information about the sample under study directly or link then entire process to an external database system.

Via the GUI, the user now tells the 'Human' cluster of modules 2 that they are to run until 12 Gigabases of Q20+ DNA sequence data have been collected. Also the modules 2 are told that they are running the same sample. The control modules 80 of each module 2 enact these commands, storing the measures of performance such as how much data has been collected and what the quality is. Other metrics may be useful for different use-cases. This control module 80 monitors the data and status of the module 2 in real-time or near-real time and is able to make decisions. In this case the control module 80 has stored the fact that it belongs to a group called 'Human' and that the group as a whole has a co-operative target of 12 Gb of Q20 data. This can be stored internally simply as a table in the memory of this process showing the module 2 name, the data generated, the target data and the quality etc or on more permanent storage, as for example Table 1.

TABLE 1

| Module 2 | Group | Group Target | Output | Internal Target | Quality | Runtime (hrs) |
|---|---|---|---|---|---|---|
| 124.45.23.1 | Human | 12 Gb | 1 Gb | 1 Gb | Q20 | 6 |
| 124.45.23.2 | Human | 12 Gb | 0.4 Gb | 1 Gb | Q20 | 6 |
| 124.45.23.3 | Human | 12 Gb | 1 Gb | 1 Gb | Q20 | 6 |
| . . . etc | | | | | | |

As shown in Table 1, each module 2 in the group 'Human' shares this table (data structure). A standard part of their operation would be to broadcast, via their internal web service 82, a copy of this table the other modules 2 at regular intervals thus synchronising them. Each module 2 can then see the status of the other modules 2 and at any time can performs a pre-scheduled operation such as the aggregation of the 'Output' column and a comparison of the total to the 'Group Target' column. Another internal computation would allow the rate of data generation of the given quality to be interpolated versus the runtime columns showing if any individual module 2, or the sum of the outputs of the module 2, are on target to meet the time requirement set by the user. Each module 2 has these computations coded into its control module 80 and each module 2 carries them out periodically on their shared and synchronised status data table. A large number of such computations have been encoded into the control module 80 covering other uses-cases than this simple example. After 6 hours it can be seen that the amount of data generated is not on track to meet the target and each module 2 is internally aware of this. One module 2 in particular appears to be performing badly. This may be for any number of reasons, but on board diagnostic information does not show any faults.

The modules 2 now make a decision based on the information they have in order to meet their targets, as discussed above. In this case the chosen course of action from all modules 2 is to increase the output of the functioning modules 2. The table was unanimous. Having internally aggregated this result the modules 2 must now calculate how much extra data is required to reach the goal. Internally they already know how much data each of them is producing per unit time, and have also obtained from the other modules 2 how much they are generating. Using pre-coded logic associated with the chosen course of action (i.e. a software function) the modules 2 now compute how much of their own output needs to be increased to meet the target. In the simplest algorithm each module 2 proposes a small increase of a certain percentage and transmits this to the other modules 2. Each module 2 then, using its internal table, calculates what effect this has on the aggregate and the target outcome. This process is repeated until all of the modules 2 show, via their internal tables, that the target can be reached.

In a more sophisticated alternative the modules 2 with lower output make proposed increments that are larger than those with good output, thus 'load sharing'. Again the same sharing of data, followed by shared computation, following by sharing a result, followed a community vote is used to allow the modules 2 to chose a collective coarse of action.

In this example the internal table has now been updated such that some modules 2 (only three shown) have increased their local performance targets from 1 Gb per day to 1.4 Gb per day to compensate for the weaker ones, as shown in Table 2. Provided nothing else changes the calculation shows that the total output for the group as whole will meet the time and quality targets. The modules 2 have thus adjusted their internal logic, with feedback from other modules 2, to meet a collective target.

TABLE 2

| Module 2 | Group | Group Target | Output | Internal Target | Quality | Runtime (hrs) |
| --- | --- | --- | --- | --- | --- | --- |
| 124.45.23.1 | Human | 12 Gb | 1 Gb | 1.4 Gb | Q20 | 6 |
| 124.45.23.2 | Human | 12 Gb | 0.4 Gb | 1 Gb | Q20 | 6 |
| 124.45.23.3 | Human | 12 Gb | 1 Gb | 1.4 Gb | Q20 | 6 |
| . . . etc | | | | | | |

Having done this the individual modules 2 must now translate collective decision making to internal remedial action. The logic to do this is coded into the control module 80. For example, sequencer temperature can be used to control the rate at which nucleotides are cleaved from the DNA strands and passed down into the nanopore. This may slightly lower the quality of the observed data (see below) if temperature is raised too high, but the basic procedure described in the steps above would detect this and seek to correct for a lowering of quality. In this case, the remedial action is higher throughput of bases. The control module 80 therefore sends a command, as a suitable function call, RPC call, or by sending a formatted string down a communication socket, to the microcontroller 58 on the internal board 50. This command instructs the microcontroller 58 to change the temperature of the analysis apparatus 13. This may be enacted by a further command being sent to a device driver controlling the thermal control element 42. The 'set' temperature of this component in increased by an increment, perhaps derived from a look up table, that is expected to increase the number of bases per unit time by the desired amount. The thermal control element 42 responds by cooling less, and sensors on-board the cartridge 10 sense the change in temperature to the desired level. This information, the recorded values, any error codes etc are transmitted back to the control module 80 which now records that the remedial action has been taken successfully.

The control module 80 has all the way through been recording and counting bases and quality scores from the data as it has been transferred from the ASIC 40 and processed by the processing module 73. This process continues and the internal tables are updated and the results transmitted to the other modules 2 in the group. All being well the instrument 1 as a whole is now on track to deliver the global performance target. If not then further action may need to be taken and other scenarios explored. These scenarios follow the same basic data flow, but would have specific logic coded into software modules accessible by the control module 80. For example, if the actions here are unable to meet the time requirements and quality requirements after adjusting temperature, the modules 2 may then decide to send a message to a user (logged at runtime) instructing that a number of extra modules 2 are required to meet the targets. This allows the user to then re-task other, perhaps idle, modules 2 and insert extra cartridges 10 with the same sample on and, in the manner described above, add them to the cluster so that they can then participate in the collective operation.

The core method is to allow collective decision making across modules 2. They each have the capability to operate alone, but can also share internal data structures about status and keep them updated. The modules 2, once aggregated and bonded into a cluster of co-operating systems, can then execute a stored protocol that responds to and/or modifies this structure. As well as allowing inter-module 2 communication this protocol triggers the execution of pre-coded logic, running on at least one embedded computer, that enables the modules 2 to modify their behaviour and to co-ordinate that modification with other modules 2.

The modules 2 cooperate to perform a biochemical analysis that is common to the modules 2 of the instrument 1. The respective biochemical analysis performed in each module 2 may be the same or different, being in general terms needing to be "common" only in the sense that global performance criteria may be set for the overall analysis. A typical example is for the biochemical analysis performed in each module 2 to be the same analysis performed on different aliquots of the same sample, or on samples that are different but perhaps related in some manner, for example sampled from a given population. Another typical example is for the biochemical analysis performed in each module 2 to be the different but related types of analysis performed on different aliquots of the same sample, or on samples that are different but perhaps related More details on the nature of the biochemical analysis that may be performed are as follows. The following paragraphs refer to numerous documents that are all incorporated by reference.

The analysis apparatus 13 described above can perform biochemical analysis using nanopores in the form of protein pores supported in an amphiphilic membrane 26.

The nature of the amphiphilic membrane 26 is as follows. For amphiphilic systems the membrane 26 is typically composed of lipid molecules or their analogues and can be either naturally occurring (e.g. phosphatidylcholine) or synthetic (DPhPC, diphytanoylphosphatidylcholine). Non-natural lipid analogues may also be used such as 1,2-dioleoyl-3-trimethylammonium-propane (DOTAP). Amphiphilic membranes may be comprised of a single species or a mixture of species. Additives such as fatty acids, fatty alcohols, cholesterol (or similar derivatives) may also be used to modulate membrane behaviour. Amphiphilic membranes provide a high resistive barrier to the flow of ions across the membrane. Further details of amphiphilic membranes that are applicable to the present invention are given in WO-2008/102121, WO-2008/102120, and WO-2009/077734.

In the analysis apparatus 13, the amphiphilic membrane 26 is formed across a well 22, but the analysis apparatus 13 can be adapted to support an amphiphilic membrane in other manners including the following. The formation of electrically addressable amphiphilic membranes can be achieved by a number of known techniques. These can be split into membranes or bilayers that are incorporated onto one or more electrodes and those that provide a divider between two or more electrodes. Membranes attached to the electrode may be bilayers or monolayers of amphiphilic species and may use direct current measurements or impedance analysis, examples of which are disclosed in (Kohli et al. Biomacromolecules. 2006; 7(12):3327-35; Andersson et al., Langmuir. 2007; 23(6):2924-7; and WO-1997/020203. Membranes dividing two or more electrodes can be formed in a number of ways including but not limited to: folded (e.g. Montal et al., Proc Natl Acad Sci USA. 1972, 69(12), 3561-3566); tip-dip (e.g. Coronado et al., Biophys. J. 1983, 43, 231-236); droplets (Holden et al., J Am Chem Soc. 2007; 129(27):8650-5; and Heron et al., Mol Biosyst. 2008; 4(12): 1191-208); glass supported (e.g. WO-2008/042018); gel-supported (e.g. WO-2008/102120); gel-encapsulated (e.g. WO 2007/127327); and tethered and porous-supported (e.g. Schmitt et al., Biophys J. 2006; 91(6):2163-71).

The nanopores are formed by protein pores or channels introduced into the amphiphilic membranes 26. The protein pores or channels may be proteins that are either natural or synthetic, examples being disclosed in WO-00/79257; WO-00/78668; U.S. Pat. No. 5,368,712; WO-1997/20203; and Holden et al., Nat Chem Biol.; 2 (6):314-8)]. Natural pores and channels may include structures where the membrane spanning portion of the protein comprises a beta-barrel, such as alpha-hemolysin (e.g. Song et al., Science. 1996; 274(5294):1859-66), OmpG (e.g. Chen et al., Proc Natl Acad Sci USA. 2008; 105(17):6272-7), OmpF (e.g. Schmitt et al., Biophys J. 2006; 91(6):2163-71) or MsPA (e.g. Butler et al., Proc Natl Acad Sci USA. 2008; 105(52): 20647-52). Alternatively, the membrane spanning portion of the protein may consist of an alpha-helix, such as a potassium channel (e.g. Holden et al., Nat Chem Biol.; 2 (6):314-8), (Syeda et al., J Am Chem Soc. 2008; 130(46):15543-8)]. The pore or channel may be a naturally occurring proteins that is modified either chemically or genetically to provide desired nanopore behaviour. An example of a chemically modified protein pore is given in WO-01/59453 and an example of a genetically modified protein pore is given in WO-99/05167. Adapters may also be added to the system to provide greater control and more targeted analyte detection, examples of which are disclosed in U.S. Pat. Nos. 6,426, 231; 6,927,070; and WO2009044170.

The nanopores allow a flow of ions to travel across the amphiphilic membrane 26. The flow of ions is modulated by pore on the basis of an analyte interaction, thus allowing the nanopore to provide a biochemical analysis. There are many examples of such modulation being used to as the basis for biochemical analysis, for example in U.S. Pat. Nos. 6,426, 231; 6,927,070; 6,426,231; 6,927,070; WO-99/05167; WO-03/095669; WO-2007/057668; WO1997020203; Clarke et al. Nat Nanotechnol. 2009; 4(4):265-270; and Stoddart et al., Proc Natl Acad Sci USA. 2009; 106(19): 7702-7707.

The analysis apparatus 13 may use nanopores for sequencing of polynucleotides, including DNA and RNA, and including naturally occurring and synthetic polynucleotides. It may apply a variety of techniques that have been proposed for deriving sequence information in a rapid and cost effective manner, typically utilising measurement of changes in the electrical signal across a single nanopore as a single strand of DNA passes through the nanopore. Such techniques include without limitation: nanopore-assisted sequencing by hydridisation; strand sequencing; and exonuclease-nanopore sequencing (e.g. D. Branton et al, Nature Biotechnology 26(10), p 1-8 (2009)). The technique may involve the polynucleotide passing through the nanopore as an intact polymer (modified or unmodified), or broken into the constituent nucleotide components or bases (for example using the techniques disclosed in: U.S. Pat. No. 5,795,782; EP-1,956,367; U.S. Pat. Nos. 6,015,714; 7,189,503; 6,627, 067; EP-1,192,453; WO-89/03432; U.S. Pat. No. 4,962,037; WO-2007/057668; International Appl. No. PCT/GB09/ 001690 (corresponding to British Appl. No. 0812693.0 and U.S. Appl. No. 61/078,687); and International Appl. No. PCT/GB09/001679 (corresponding to British Appl. No. 0812697.1 and U.S. Appl. No. 61/078,695).

In general, present invention may be applied to any apparatus providing the measurement of nanopores by providing two electrodes, one either side of an insulating membrane, into which a nanopore is inserted. When immersed in an ionic solution, a biased potential between the electrodes will drive ionic flow through the nanopore that can be measured as current in an external electrical circuit. This current alters as DNA passes through the nanopore, and with sufficient resolution, the constituent bases can be recognised from the changes, for example as disclosed in Clarke et al. Nat Nanotechnol. 2009; 4(4):265-270; International Appl. No. PCT/GB09/001690 (corresponding to British Appl. No. 0812693.0 and U.S. Appl. No. 61/078, 687); and D. Stoddart, PNAS doi 10.1073/pnas.0901054106, April 2009.

Further, the present invention may be applied to any apparatus in which arrays of nanopores measure the same sample by providing individually addressable electrodes on one side of each nanopore in the array connected to either a common electrode or an equivalent number of addressable electrodes in the sample on the other side. External circuitry can then perform measurements of DNA passing through each and every nanopore in the array without the synchronisation of base addition to each nanopore in the array, i.e. each nanopore is free to process a single DNA strand independently of every other, for example as disclosed in US-2009/0167288; WO-2009/077734; and U.S. Application No. 61/170,729. Having processed one strand, each nanopore is also then free to begin processing a subsequent strand.

One advantage of nanopore-based analysis is that the quality of measurement does not change over time for a fully-functioning nanopore, i.e. the accuracy of base identification is the same at the start of sequencing as at any point in the future, subject to the expect experimental limitations. This enables each sensor to perform, at constant average quality, multiple analyses in a sequential fashion on the same sample or on multiple samples over time.

Besides sequencing of polynucleotides, the nanopores may be applied to a diverse range of other biochemical analysis, including without limitation: diagnostics (e.g. Howorka et al., Nat Biotechnol. 2001; 19(7):636-9); protein detection (e.g. Cheley et al., Chembiochem. 2006; 7(12): 1923-7; and Shim et al., J Phys Chem B. 2008; 112(28): 8354-60); drug molecule analysis (e.g. Kang et al., J Am Chem Soc. 2006; 128(33):10684-5); ion channel screening (e.g. Syeda et al., J Am Chem Soc. 2008 Nov. 19; 130(46): 15543-8), defence (e.g. Wu et al., J Am Chem Soc. 2008; 130(21):6813-9; and Guan et al., Chembiochem. 2005; 6(10):1875-81); and polymers (e.g. Gu et al., Biophys. J. 2000; 79, 1967-1975; Movileanu et al., Biophys. J. 2005; 89, 1030-1045; and Maglia et al., Proc Natl Acad Sci USA. USA 2008; 105, 19720-19725).

The present invention may also be applied to an analysis apparatus in which nanopores are provided in solid state membranes. In this case the nanopore is a physical pore in a membrane formed from a solid material. Such membranes have many advantages over fluid or semi-fluid layers, particularly with respect to stability and size. The original concept was proposed by researchers at the University of Harvard for examining polymers, such as DNA (e.g. WO-00/79257; and WO 00/78668). Since then the work has expanded to include the following techniques that may be applied in the present invention: fabrication methods (e.g. WO-03/003446; U.S. Pat. No. 7,258,838; WO-2005/000732; WO-2004/077503; WO-2005/035437; WO-2005/061373); data acquisition and evaluation (e.g. WO-01/59684; WO-03/000920; WO-2005/017025; and WO-2009/045472), incorporation of nanotubes (e.g. WO-2005/000739; WO-2005/124888; WO-2007/084163); and the addition of molecular motors (e.g. WO-2006/028508); the use of field effect transistors or similar embedded within nanopore structures (e.g. U.S. Pat. Nos. 6,413,792, 7,001,792); the detection of fluorescent probes interacting with a nanopore or nanochannel (e.g. U.S. Pat. No. 6,355,420; WO-98/35012); and the illumination and detection of fluorescent probes being removed from their target substrates as they translocate a nanopore (e.g. US-2009-0029477). Even the use of mass spectrometry may be employed in the analysis apparatus, for example as a polymer of interest passes through a nanopore or channel and whose monomers are then cleaved and ionised sequentially analysed using mass spectrometry.

The present invention may also be applied to an analysis apparatus which is arranged to perform a sequencing of polynucleotides using techniques other than nanopores, for example: using stepwise cyclical chemistry, followed by an imaging stage to detect the incorporation, annealing or removal of chemically labelled fluorescent probes that enable the polynucleotide under study to be decoded; techniques that measure the activity of DNA-handling enzymes in real time, including the measurement of DNA polymerase activity in zero-mode waveguides (e.g. Levene et al., "Zero-Mode Waveguides for Single-Molecule Analysis at High Concentrations", Science 299:682-686; Eid et al., "Real-Time DNA Sequencing from Single Polymerase Molecules", Science 323:133-138; U.S. Pat. Nos. 7,170,050; 7,476,503); techniques that measure energy emissions provided by fluorescent emission transfer between suitable chemical groups provided on both of the polymerase and incorporated DNA bases (e.g. U.S. Pat. No. 7,329,492), for example using activated quantum dots attached to polymerases acting on DNA wherein DNA bases being incorporated into a newly synthesised strand containing fluorescent groups are energised in the presence of such activated quantum dots; or techniques that use ion-sensitive FET's to measure local changes in ions (e.g. pH) to infer chemical activity as DNA bases are incorporated into a new strand (e.g. WO-2008/076406).

The present invention may also be applied to an analysis apparatus which is arranged to perform other types of biochemical analysis that do not use nanopores, some examples of which are as follows. The present invention may also be applied to an analysis apparatus which is arranged to perform other types of biochemical analysis that do not use nanopores, including, but not limited to:
1) Ion channel screening;
2) Real time DNA amplification (PCR, RCA, NASBA);
3) Enzyme activity by measurement of reactant or product changes, including
   a. Glucose oxidase,
   b. G-coupled protein receptors,
   c. Fluorescent Protein gene activation;
4) Surface Plasmon Resonance monitored reactions, including kinetic binding of ligands to target molecules (e.g. proteins to chemical inhibitors);
5) DNA microarrays for transcriptome analysis or infectious disease identification;
6) Antibody array chips for measuring proteins in samples or solutions; or
7) Protein binding array chips monitoring kinetics of interactions of proteins with substrates, targets, ligands etc using fluorescent or electromagnetic readouts.

In each case a variety of experimental parameters may be varied in order to meet a user's global requirements for the experiment, including temperature, time of experiment, rates of sampling of readout, intensity of light or degree of electrical potential, pH or ionic strength.

The analysis may be a chemical or biological assay, and could be used to carry out biomarker validation studies, clinical tests and high-throughput screening. These tests may involve carrying out chromatography (HPLC (high performance liquid chromatography, TLC (thin layer chromatography), FPLC (fast protein liquid chromatography), flash chromatography, with detection of analyte in the liquid eluent (by absorbance, fluorescence, radiometric methods, light scattering, particle analysis, mass spectrometry), or an immunoassay or using direct mass spectrometry (MALDI (matrix assisted laser desorption ionization), APCI (atmospheric pressure chemical ionization), ESI (electrospray ionization) ionization with Quadrupole (single and multiple), time-of-flight, ion trap detection). Immunoassays include an ELISA (enzyme-linked immunosorbent assay), lateral flow assay, radioimmunoassay, magnetic immunoassay or immunofluorescence assay.

These tests and assays can be used in the context of: identification of foetal abnormalities such as Down's Syndrome, genome-wide association studies, pharmacokinetic and pharmacodynamic investigations on tissues and whole animals, drug testing in sport, testing for micro-organisms in environmental matrices (sewage, polluted water etc.), testing for hormones and growth factors in treated water and so on.

The analysis may be applied to biomarker validation studies. The present invention can allow very high numbers of samples to be analysed quickly and easily. For example, the current process of biomarker discovery is hampered by the validation step, ie. once a candidate marker has been found, large numbers of samples must be examined in order to statistically confirm its altered levels in the tissues of interest. An assay must therefore be developed for each marker. The system of the present invention has a single readout for all analytes, for example DNA, RNA, protein or small molecule, cutting down on the assay development stages.

The analysis may be applied to clinical tests and ELISA substitute. When a sample is submitted for tests at a hospital or clinic, the testing procedure is very likely to involve either mass spectrometry or ELISA. Both of these can be supplanted by the system of the present invention. Development of suitable tests on the system of the invention will give huge increases in throughput and savings in sample preparation time and handling. This will apply to large proteins such as growth factors, peptides such as insulin, or small molecules such as drugs of abuse or prescription drugs.

The analysis may be applied to high-throughput screening. Any quantitative screen can be carried out on the system of the present invention. Thus, if an assay (for example a protease assay) that gives a peptide or small molecule as a product is currently used in high-throughput screening, the present invention can increase the throughput and cut down on sample handling and preparation time.

The invention claimed is:

1. A system comprising:
   i) a module for performing a biochemical analysis of a sample, wherein the module is configured to perform said biochemical analysis based on a plurality of operational parameters that each affect performance of the module in performing the biochemical analysis, the module comprising:
      an analysis apparatus that is capable of supporting plural nanopores and being operable to perform the biochemical analysis of the sample using the nanopores, the analysis apparatus comprising electrodes arranged to generate an electrical signal across each nanopore; and
      a signal processing circuit arranged to generate output data representing results of the biochemical analysis of the sample, said generation being based on the electrical signals generated from the electrodes of the analysis apparatus; and
   ii) a control unit configured to control the operation of the module on the basis of a performance target, wherein the control unit is configured to:
      receive the output data generated by the signal processing circuit of the module;
      determine, at least once during the biochemical analysis of the sample using the nanopores, one or more measures of performance of the biochemical analysis based on the output data generated by the signal processing circuit of the module; and
      adjust at least one of the operational parameters of the module at least once during the biochemical analysis of the sample by the module based on the one or more measures of performance and the performance target.

2. A system according to claim 1, wherein the measures of performance and the performance target represent at least one of:
   a time within which the output data is produced;
   a quantity of the output data that is produced; or
   a quality of the output data that is produced.

3. A system according to claim 1, wherein the plurality of operational parameters of the module include at least one of:
   the temperature of the analysis apparatus;
   electrical parameters of the biochemical analysis;
   fluidics parameters of the analysis apparatus; or
   sampling characteristics of the output data.

4. A system according to claim 1, wherein the biochemical analysis is analysis of a molecule in the sample.

5. A system according to claim 4, wherein the molecule is a polymer.

6. A system according to claim 5, wherein the polymer is a polynucleotide.

7. A system according to claim 6, wherein the biochemical analysis is sequencing of a polynucleotide in the sample, the output data including output sequence data representing a sequence of the polynucleotide.

8. A system according to claim 1, wherein the signal processing circuit is arranged to detect events occurring at the nanopores from the electrical signals across each nanopore, and to generate output data representing those events.

9. A system according to claim 1, wherein the analysis apparatus is capable of forming amphiphilic membranes and supporting the plural nanopores therein.

10. A system according to claim 1, wherein the control unit is arranged to determine measures of performance of the biochemical analysis and to adjust operational parameters of the module based on the measures of performance repeatedly during the biochemical analysis.

11. A system according to claim 1, wherein adjusting the at least one of the operational parameters of the module affects operation of the analysis apparatus.

12. A system according to claim 11, wherein adjusting the at least one of the operational parameters of the module affects the operation of the signal processing circuit.

13. A system according to claim 1, excluding the case that:
   the signal processing circuit comprises a plurality of detection channels each capable of amplifying an electrical signal from across one of the nanopores, the analysis apparatus being capable of supporting a number of nanopores greater than the number of detection channels;
   the module comprises a switch arrangement capable of selectively connecting the detection channels to receive electrical signals across respective nanopores; and
   the control unit is arranged to vary the operation of the module by controlling the switching arrangement to selectively connect the detection channels to respective sensor elements that have acceptable performance on the basis of the amplified electrical signals that are output from the detection channels.

14. A system according to claim 1, wherein the control unit is configured to determine measures of performance of the biochemical analysis and to adjust operational parameters of the module based on the measures of performance continuously during the biochemical analysis.

15. A system according to claim 1, wherein the module is configured to communicate with the control unit and/or with at least one other module, at least once during the biochemical analysis, the measures of performance, such that the performance of the module and of at least one other module is analyzable by the control unit.

16. A system according to claim 15,
   wherein the module is configured to receive a performance target to determine a local performance target, which local performance target is configured to be varied by the performance target based on the communicated measures of performance to produce an updated local performance target; and
   wherein the module is configured to operate in accordance with the updated local performance target.

17. A system according to claim 1,
   wherein the performance target includes a local performance target; and
   wherein operation of the module is configured to be performed on the basis of a local performance target for that module, wherein determining measures of performance involves calculating the measures of performance from data output from a control operation, such that the module is configured to perform a local control process independently.

18. A system according to claim 1,
   wherein the performance target includes a local performance target;
   wherein the module is configured to cooperate with another module to determine the respective local performance targets of each module; and
   wherein the module is configured to derive its own local performance target, to communicate its own local performance target to another module, to receive a local performance target from another module, to determine whether the performance target is met and, if necessary, to revise its local performance target.

* * * * *